US011464423B2

(12) United States Patent
Hafezi et al.

(10) Patent No.: US 11,464,423 B2
(45) Date of Patent: Oct. 11, 2022

(54) IN-BODY POWER SOURCE HAVING HIGH SURFACE AREA ELECTRODE

(71) Applicant: OTSUKA PHARMACEUTICAL CO. LTD., Tokyo (JP)

(72) Inventors: Hooman Hafezi, Redwood City, CA (US); Timothy Robertson, Belmont, CA (US); Eric Snyder, South San Francisco, CA (US); Brad Cozad, Newark, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 944 days.

(21) Appl. No.: 14/602,895

(22) Filed: Jan. 22, 2015

(65) Prior Publication Data

US 2015/0230728 A1 Aug. 20, 2015

Related U.S. Application Data

(63) Continuation of application No. 12/527,190, filed as application No. PCT/US2008/053999 on Feb. 14, 2008, now Pat. No. 8,956,288.

(Continued)

(51) Int. Cl.
*A61B 5/00* (2006.01)
*H01M 4/00* (2006.01)
(Continued)

(52) U.S. Cl.
CPC ............ *A61B 5/073* (2013.01); *A61B 5/0028* (2013.01); *A61J 3/07* (2013.01); *A61M 31/00* (2013.01);
(Continued)

(58) Field of Classification Search
None
See application file for complete search history.

(56) References Cited

U.S. PATENT DOCUMENTS 3,218,638 A 11/1965 Honig
3,345,989 A 10/1967 Reynolds
(Continued)

FOREIGN PATENT DOCUMENTS

CA 2953847 11/2006
CN 2748032 12/2005
(Continued)

OTHER PUBLICATIONS

Van der Biest, O. et al; "Electrophoretic deposition of materials"; Annu. Rev. Mater. Sci. 1999. 29:327-52. (Year: 1999).*
(Continued)

*Primary Examiner* — Lori A. Clow
*Assistant Examiner* — Marie Archer
(74) *Attorney, Agent, or Firm* — Pillsbury Winthrop Shaw Pittman, LLP

(57) ABSTRACT

Power sources that enable in-body devices, such as implantable and ingestible devices, are provided. Aspects of the in-body power sources of the invention include a solid support, a first high surface area electrode and a second electrode. Embodiments of the in-power sources are configured to emit a detectable signal upon contact with a target physiological site. Also provided are methods of making and using the power sources of the invention.

19 Claims, 2 Drawing Sheets

Related U.S. Application Data

(60) Provisional application No. 60/889,870, filed on Feb. 14, 2007.

(51) Int. Cl.

| | |
|---|---|
| ***A61B 5/07*** | (2006.01) |
| ***A61J 3/07*** | (2006.01) |
| ***H01M 8/08*** | (2016.01) |
| ***H01M 4/02*** | (2006.01) |
| ***H01M 6/34*** | (2006.01) |
| ***H01M 4/66*** | (2006.01) |
| ***A61M 31/00*** | (2006.01) |
| ***C23C 14/32*** | (2006.01) |
| ***C25D 9/04*** | (2006.01) |
| ***C25D 13/02*** | (2006.01) |
| ***H01M 4/04*** | (2006.01) |
| ***H01M 10/04*** | (2006.01) |
| *A61N 1/378* | (2006.01) |

(52) U.S. Cl.

CPC .............. *C23C 14/325* (2013.01); *C25D 9/04* (2013.01); *C25D 13/02* (2013.01); *H01M 4/02* (2013.01); *H01M 4/0416* (2013.01); *H01M 4/0426* (2013.01); *H01M 4/668* (2013.01); *H01M 6/34* (2013.01); *H01M 8/08* (2013.01); *H01M 10/0436* (2013.01); *A61B 2560/0214* (2013.01); *A61B 2560/04* (2013.01); *A61B 2562/12* (2013.01); *A61N 1/378* (2013.01); *G08C 2200/00* (2013.01)

(56) References Cited

U.S. PATENT DOCUMENTS

| | | | | |
|---|---|---|---|---|
| 3,353,539 | A | | 11/1967 | Preston |
| 3,409,721 | A | | 11/1968 | Applezweig |
| 3,419,736 | A | | 12/1968 | Walsh |
| 3,589,943 | A | | 6/1971 | Grubb et al. |
| 3,607,788 | A | | 9/1971 | Adolph |
| 3,628,669 | A | | 12/1971 | McKinnis et al. |
| 3,642,008 | A | | 2/1972 | Bolduc |
| 3,679,480 | A | | 7/1972 | Brown et al. |
| 3,682,160 | A | | 8/1972 | Murata |
| 3,719,183 | A | | 3/1973 | Schwartz |
| 3,727,616 | A | | 4/1973 | Lenzkes |
| 3,799,802 | A | | 3/1974 | Schneble, Jr. et al. |
| 3,825,016 | A | | 7/1974 | Lale et al. |
| 3,828,766 | A | | 8/1974 | Krasnow |
| 3,837,339 | A | | 9/1974 | Aisenberg et al. |
| 3,893,111 | A | | 7/1975 | Cotter |
| 3,944,064 | A | | 3/1976 | Bashaw et al. |
| 3,967,202 | A | | 6/1976 | Batz |
| 3,989,050 | A | | 11/1976 | Buchalter |
| 4,017,856 | A | | 4/1977 | Wiegand |
| 4,055,178 | A | | 10/1977 | Harrigan |
| 4,062,750 | A | | 12/1977 | Butler |
| 4,077,397 | A | | 3/1978 | Ellis |
| 4,077,398 | A | | 3/1978 | Ellis |
| 4,082,087 | A | | 4/1978 | Howson |
| 4,090,752 | A | | 5/1978 | Long |
| 4,105,023 | A | | 8/1978 | Merchese et al. |
| 4,106,348 | A | | 8/1978 | Auphan |
| 4,129,125 | A | | 12/1978 | Lester |
| 4,133,730 | A | * | 1/1979 | Du Bois ................. C22C 14/00 204/254 |
| 4,141,349 | A | | 2/1979 | Ory et al. |
| 4,166,453 | A | | 9/1979 | McClelland |
| 4,239,046 | A | | 12/1980 | Ong |
| 4,251,795 | A | | 2/1981 | Shibasaki et al. |
| 4,269,189 | A | | 5/1981 | Abraham |
| 4,281,664 | A | | 8/1981 | Duggan |
| 4,331,654 | A | | 5/1982 | Morris |
| 4,345,588 | A | | 8/1982 | Widder et al. |
| 4,418,697 | A | | 12/1983 | Tama |
| 4,425,117 | A | | 1/1984 | Hugemann |
| 4,439,196 | A | | 3/1984 | Higuchi |
| 4,494,950 | A | | 1/1985 | Fischell |
| 4,526,474 | A | | 7/1985 | Simon |
| 4,547,391 | A | * | 10/1985 | Jenkins ................... B05B 7/224 219/121.11 |
| 4,559,950 | A | | 12/1985 | Vaughan |
| 4,564,363 | A | | 1/1986 | Bagnall et al. |
| 4,578,061 | A | | 3/1986 | Lemelson |
| 4,618,533 | A | | 10/1986 | Steuck |
| 4,635,641 | A | | 1/1987 | Hoffman |
| 4,654,165 | A | | 3/1987 | Eisenber |
| 4,663,250 | A | | 5/1987 | Ong et al. |
| 4,669,479 | A | | 6/1987 | Dunseath |
| 4,681,111 | A | | 7/1987 | Silvian |
| 4,687,660 | A | | 8/1987 | Baker et al. |
| 4,725,997 | A | | 2/1988 | Urquhart et al. |
| 4,749,575 | A | | 6/1988 | Rotman et al. |
| 4,763,659 | A | | 8/1988 | Dunseath |
| 4,767,627 | A | | 8/1988 | Caldwell et al. |
| 4,784,162 | A | | 11/1988 | Ricks |
| 4,793,825 | A | | 12/1988 | Benjamin et al. |
| 4,809,705 | A | | 3/1989 | Ascher |
| 4,835,373 | A | | 5/1989 | Adams et al. |
| 4,844,076 | A | | 7/1989 | Lesho |
| 4,871,974 | A | | 10/1989 | Davis et al. |
| 4,876,093 | A | | 10/1989 | Theeuwes et al. |
| 4,896,261 | A | | 1/1990 | Nolan |
| 4,975,230 | A | | 12/1990 | Pinkhasov |
| 4,987,897 | A | | 1/1991 | Funke |
| 5,000,957 | A | | 3/1991 | Eckenhoff et al. |
| 5,016,634 | A | | 5/1991 | Vock et al. |
| 5,079,006 | A | | 1/1992 | Urguhart |
| 5,167,626 | A | | 12/1992 | Casper |
| 5,176,626 | A | | 1/1993 | Soehendra |
| 5,179,578 | A | | 1/1993 | Ishizu |
| 5,245,332 | A | | 9/1993 | Katzenstein et al. |
| 5,261,402 | A | | 11/1993 | DiSabito |
| 5,263,481 | A | | 11/1993 | Axelgaard et al. |
| 5,276,710 | A | | 1/1994 | Iwasaki |
| 5,279,607 | A | | 1/1994 | Schentag et al. |
| 5,281,287 | A | | 1/1994 | Lloyd |
| 5,283,136 | A | | 2/1994 | Peled et al. |
| 5,288,564 | A | | 2/1994 | Klein |
| 5,305,745 | A | | 4/1994 | Zacouto |
| 5,318,557 | A | | 6/1994 | Gross |
| 5,394,882 | A | | 3/1995 | Mawhinney |
| 5,395,366 | A | | 3/1995 | D'Andrea et al. |
| 5,411,535 | A | | 5/1995 | Fujii et al. |
| 5,412,372 | A | | 5/1995 | Parkhurst et al. |
| 5,428,961 | A | | 7/1995 | Sakakibara |
| 5,436,091 | A | | 7/1995 | Shackle et al. |
| 5,443,461 | A | | 8/1995 | Atkinson et al. |
| 5,443,843 | A | | 8/1995 | Curatolo et al. |
| 5,458,141 | A | | 10/1995 | Neil et al. |
| 5,468,222 | A | | 11/1995 | Altchuler |
| 5,485,841 | A | | 1/1996 | Watkin et al. |
| 5,511,548 | A | | 4/1996 | Riazzi et al. |
| 5,538,007 | A | | 7/1996 | Gorman |
| 5,551,953 | A | | 9/1996 | Lattin et al. |
| 5,567,210 | A | | 10/1996 | Bates et al. |
| 5,596,302 | A | | 1/1997 | Mastrocola et al. |
| D377,983 | S | | 2/1997 | Sabri et al. |
| 5,600,548 | A | | 2/1997 | Nguyen et al. |
| 5,634,466 | A | | 6/1997 | Gruner |
| 5,634,468 | A | | 6/1997 | Platt |
| 5,638,406 | A | | 6/1997 | Sogabe |
| 5,645,063 | A | | 7/1997 | Straka et al. |
| 5,705,189 | A | | 1/1998 | Lehmann et al. |
| 5,720,771 | A | | 2/1998 | Snell |
| 5,738,708 | A | | 4/1998 | Peachey et al. |
| 5,740,811 | A | | 4/1998 | Hedberg |
| 5,757,326 | A | | 5/1998 | Koyama et al. |
| 5,792,048 | A | | 8/1998 | Schaefer |
| 5,802,467 | A | | 9/1998 | Salazar |
| 5,833,716 | A | | 11/1998 | Bar-Or |
| 5,836,474 | A | | 11/1998 | Wessberg |
| 5,845,265 | A | | 12/1998 | Woolston |

(56) References Cited

U.S. PATENT DOCUMENTS 5,862,803 A 1/1999 Besson
5,862,808 A 1/1999 Albarello
5,868,136 A 2/1999 Fox
5,914,701 A 6/1999 Gersheneld et al.
5,917,346 A 6/1999 Gord
5,921,925 A 7/1999 Cartmell et al.
5,925,030 A 7/1999 Gross et al.
5,925,066 A 7/1999 Kroll et al.
5,957,854 A 9/1999 Besson et al.
5,963,132 A 10/1999 Yoakum et al.
5,965,629 A 10/1999 Jung et al.
5,974,124 A 10/1999 Schlueter, Jr. et al.
5,981,166 A 11/1999 Mandecki
5,999,846 A 12/1999 Pardey et al.
6,009,350 A 12/1999 Renken
6,023,631 A 2/2000 Cartmell et al.
6,038,464 A 3/2000 Axelgaard et al.
6,042,710 A 3/2000 Dubrow
6,047,203 A 4/2000 Sackner
6,076,016 A 6/2000 Feierbach et al.
6,081,734 A 6/2000 Batz
6,083,248 A 7/2000 Thompson
6,090,489 A 7/2000 Hayakawa et al.
6,091,975 A 7/2000 Daddona et al.
6,095,985 A 8/2000 Raymond et al.
6,099,482 A 8/2000 Brune et al.
6,115,636 A 9/2000 Ryan
6,117,077 A 9/2000 Del Mar et al.
6,122,351 A 9/2000 Schlueter, Jr. et al.
6,141,592 A 10/2000 Pauly
6,149,940 A 11/2000 Maggi et al.
6,200,265 B1 3/2001 Walsh et al.
6,204,764 B1 3/2001 Maloney
6,206,702 B1 3/2001 Hayden et al.
6,217,744 B1 4/2001 Crosby
6,231,593 B1 5/2001 Meserol
6,245,057 B1 6/2001 Sieben et al.
6,269,058 B1 7/2001 Yamanoi et al.
6,275,476 B1 8/2001 Wood
6,285,897 B1 9/2001 Kilcoyne et al.
6,287,252 B1 9/2001 Lugo
6,288,629 B1 9/2001 Cofino et al.
6,289,238 B1 9/2001 Besson et al.
6,315,719 B1 11/2001 Rode et al.
6,342,774 B1 1/2002 Kreisinger et al.
6,344,824 B1 2/2002 Takasugi et al.
6,358,202 B1 3/2002 Arent
6,364,834 B1 4/2002 Reuss
6,366,206 B1 4/2002 Ishikawa et al.
6,368,190 B1 4/2002 Easter et al.
6,371,927 B1 4/2002 Brune
6,374,670 B1 4/2002 Spelman
6,380,858 B1 4/2002 Yarin et al.
6,390,088 B1 5/2002 Noehl et al.
6,394,953 B1 5/2002 Devlin et al.
6,394,997 B1 5/2002 Lemelson
6,409,674 B1 6/2002 Brockway et al.
6,411,567 B1 6/2002 Niemiec et al.
6,426,863 B1 7/2002 Munshi
6,432,292 B1 8/2002 Pinto et al.
6,440,069 B1 8/2002 Raymond et al.
6,441,747 B1 8/2002 Khair
6,453,199 B1 9/2002 Kobozev
6,477,424 B1 11/2002 Thompson et al.
6,482,156 B2 11/2002 Lliff
6,494,829 B1 12/2002 New et al.
6,496,705 B1 12/2002 Ng et al.
6,505,077 B1 1/2003 Kast et al.
6,525,996 B1 2/2003 Miyazawa
6,526,315 B1 2/2003 Inagawa
6,531,026 B1 3/2003 Takeichi et al.
6,540,699 B1 4/2003 Smith
6,544,174 B2 4/2003 West
6,564,079 B1 5/2003 Cory
6,572,636 B1 6/2003 Hagen et al.
6,574,425 B1 6/2003 Weiss et al.
6,577,893 B1 6/2003 Besson et al.
6,579,231 B1 6/2003 Phipps
6,595,929 B2 7/2003 Stivoric
6,599,284 B2 7/2003 Faour et al.
6,605,038 B1 8/2003 Teller
6,605,046 B1 8/2003 Del Mar
6,609,018 B2 8/2003 Cory
6,612,984 B1 9/2003 Kerr
6,632,175 B1 10/2003 Marshall
6,632,216 B2 10/2003 Houzego et al.
6,635,279 B2 10/2003 Kolter et al.
6,638,231 B2 10/2003 Govari et al.
6,643,541 B2 11/2003 Mok et al.
6,650,718 B1 11/2003 Fujimura et al.
6,654,638 B1 11/2003 Sweeney
6,663,846 B1 12/2003 McCombs
6,673,474 B2 1/2004 Yamamoto
6,679,830 B2 1/2004 Kolarovic et al.
6,680,923 B1 1/2004 Leon
6,683,493 B1 1/2004 Fujimora et al.
6,689,117 B2 2/2004 Sweeney et al.
6,694,161 B2 2/2004 Mehrotra
6,704,602 B2 3/2004 Berg et al.
6,720,923 B1 4/2004 Hayward et al.
6,738,671 B2 5/2004 Christophersom et al.
6,740,033 B1 5/2004 Olejniczak et al.
6,745,082 B2 6/2004 Axelgaard et al.
6,755,783 B2 6/2004 Cosentino
6,757,523 B2 6/2004 Fry
6,759,968 B2 7/2004 Zierolf
6,771,174 B2 8/2004 Broas
6,773,429 B2 8/2004 Sheppard et al.
6,800,060 B2 10/2004 Marshall
6,801,137 B2 10/2004 Eggers et al.
6,804,558 B2 10/2004 Haller et al.
6,814,706 B2 11/2004 Barton et al.
6,822,554 B2 11/2004 Vrijens et al.
6,836,862 B1 12/2004 Erekson et al.
6,839,659 B2 1/2005 Tarassenko et al.
6,840,904 B2 1/2005 Goldberg
6,842,636 B2 1/2005 Perrault
6,845,272 B1 1/2005 Thomsen
6,864,780 B2 3/2005 Doi
6,879,810 B2 4/2005 Bouet
6,882,881 B1 4/2005 Lesser et al.
6,897,788 B2 5/2005 Khair et al.
6,909,878 B2 6/2005 Haller
6,922,592 B2 7/2005 Thompson et al.
6,928,370 B2 8/2005 Anuzis et al.
6,929,636 B1 8/2005 Von Alten
6,937,150 B2 8/2005 Medema
6,939,292 B2 9/2005 Mizuno
6,942,616 B2 9/2005 Kerr
6,951,536 B2 10/2005 Yokoi
6,957,107 B2 10/2005 Rogers et al.
6,959,929 B2 11/2005 Pugnet et al.
6,968,153 B1 11/2005 Heinonen
6,987,965 B2 1/2006 Ng et al.
6,990,082 B1 1/2006 Zehavi et al.
7,002,476 B2 2/2006 Rapchak
7,004,395 B2 2/2006 Koenck
7,009,634 B2 3/2006 Iddan et al.
7,009,946 B1 3/2006 Kardach
7,013,162 B2 3/2006 Gorsuch
7,016,648 B2 3/2006 Haller
7,020,508 B2 3/2006 Stivoric
7,023,940 B2 4/2006 Nakamura et al.
7,024,248 B2 4/2006 Penner et al.
7,031,745 B2 4/2006 Shen
7,031,857 B2 4/2006 Tarassenko et al.
7,039,453 B2 5/2006 Mullick
7,044,911 B2 5/2006 Drinan et al.
7,046,649 B2 5/2006 Awater et al.
7,050,419 B2 5/2006 Azenkot et al.
7,062,308 B1 6/2006 Jackson
7,069,062 B2 6/2006 Minotani et al.
7,076,437 B1 7/2006 Levy
7,081,693 B2 7/2006 Hamel et al.

(56) References Cited

U.S. PATENT DOCUMENTS 7,091,726 B2 8/2006 Sano et al.
7,118,531 B2 10/2006 Krill
7,125,382 B2 10/2006 Zhou et al.
7,127,300 B2 10/2006 Mazar et al.
7,146,228 B2 12/2006 Nielsen
7,146,449 B2 12/2006 Do et al.
7,149,581 B2 12/2006 Goedeke et al.
7,154,071 B2 12/2006 Sattler et al.
7,155,232 B2 12/2006 Godfrey et al.
7,160,258 B2 1/2007 Imran
7,161,484 B2 1/2007 Tsoukalis
7,164,942 B2 1/2007 Avrahami
7,171,166 B2 1/2007 Ng et al.
7,171,177 B2 1/2007 Park et al.
7,171,259 B2 1/2007 Rytky
7,176,784 B2 2/2007 Gilbert et al.
7,187,960 B2 3/2007 Abreu
7,188,767 B2 3/2007 Penuela
7,194,038 B1 3/2007 Inkinen
7,206,630 B1 4/2007 Tarler
7,209,790 B2 4/2007 Thompson et al.
7,215,660 B2 5/2007 Perlman
7,215,991 B2 5/2007 Besson
7,218,967 B2 5/2007 Bergelson
7,231,451 B2 6/2007 Law
7,243,118 B2 7/2007 Lou
7,246,521 B2 7/2007 Kim
7,249,212 B2 7/2007 Do
7,252,792 B2 8/2007 Perrault
7,253,716 B2 8/2007 Lovoi et al.
7,261,690 B2 8/2007 Teller
7,270,633 B1 9/2007 Goscha
7,273,454 B2 9/2007 Raymond et al.
7,285,090 B2 10/2007 Stivoric et al.
7,289,855 B2 10/2007 Nghiem
7,291,014 B2 11/2007 Chung et al.
7,291,497 B2 11/2007 Holmes
7,292,139 B2 11/2007 Mazar et al.
7,294,105 B1 11/2007 Islam
7,295,877 B2 11/2007 Govari
7,311,665 B2 12/2007 Hawthorne
7,313,163 B2 12/2007 Liu
7,317,378 B2 1/2008 Jarvis et al.
7,318,808 B2 1/2008 Tarassenko et al.
7,336,732 B1 2/2008 Wiss
7,336,929 B2 2/2008 Yasuda
7,342,895 B2 3/2008 Serpa
7,346,380 B2 3/2008 Axelgaard et al.
7,349,722 B2 3/2008 Witkowski et al.
7,352,998 B2 4/2008 Palin
7,353,258 B2 4/2008 Washburn
7,357,891 B2 4/2008 Yang et al.
7,359,674 B2 4/2008 Markki
7,366,558 B2 4/2008 Virtanen et al.
7,366,675 B1 4/2008 Walker et al.
7,368,190 B2 5/2008 Heller et al.
7,368,191 B2 5/2008 Andelman et al.
7,373,196 B2 5/2008 Ryu et al.
7,375,739 B2 5/2008 Robbins
7,376,435 B2 5/2008 McGowan
7,382,247 B2 6/2008 Welch et al.
7,382,263 B2 6/2008 Danowski et al.
7,387,607 B2 6/2008 Holt
7,388,903 B2 6/2008 Godfrey et al.
7,389,088 B2 6/2008 Kim
7,392,015 B1 6/2008 Farlow
7,395,106 B2 7/2008 Ryu et al.
7,396,330 B2 7/2008 Banet
7,404,968 B2 7/2008 Abrams et al.
7,413,544 B2 8/2008 Kerr
7,414,534 B1 8/2008 Kroll et al.
7,414,543 B2 8/2008 Rye et al.
7,415,242 B1 8/2008 Ngan
7,419,468 B2 9/2008 Shimizu et al.
7,424,268 B2 9/2008 Diener
7,424,319 B2 9/2008 Muehlsteff
7,427,266 B2 9/2008 Ayer et al.
7,433,731 B2 10/2008 Matsumura et al.
7,462,150 B1 12/2008 Bharmi
7,471,665 B2 12/2008 Perlman
7,485,093 B2 2/2009 Glukhovsky
7,485,095 B2 2/2009 Shusterman
7,499,674 B2 3/2009 Salokannel
7,502,643 B2 3/2009 Farringdon et al.
7,505,795 B1 3/2009 Lim et al.
7,508,248 B2 3/2009 Yoshida
7,510,121 B2 3/2009 Koenck
7,512,448 B2 3/2009 Malick
7,512,860 B2 3/2009 Miyazaki et al.
7,515,043 B2 4/2009 Welch
7,519,416 B2 4/2009 Sula et al.
7,523,756 B2 4/2009 Minai
7,525,426 B2 4/2009 Edelstein
7,539,533 B2 5/2009 Tran
7,542,878 B2 6/2009 Nanikashvili
7,547,278 B2 6/2009 Miyazaki et al.
7,551,590 B2 6/2009 Haller
7,554,452 B2 6/2009 Cole
7,558,620 B2 7/2009 Ishibashi
7,558,622 B2 7/2009 Tran
7,558,965 B2 7/2009 Wheeler et al.
7,575,005 B2 8/2009 Mumford
7,614,743 B2 11/2009 Geiger
7,616,111 B2 11/2009 Covannon
7,616,710 B2 11/2009 Kim et al.
7,617,001 B2 11/2009 Penner et al.
7,639,473 B2 12/2009 Hsu et al.
7,640,802 B2 1/2010 King et al.
7,647,112 B2 1/2010 Tracey
7,647,185 B2 1/2010 Tarassenko et al.
7,653,031 B2 1/2010 Godfrey et al.
7,668,437 B1 2/2010 Yamada et al.
7,683,761 B2 2/2010 Burghard et al.
7,672,703 B2 3/2010 Yeo et al.
7,672,714 B2 3/2010 Kuo
7,673,679 B2 3/2010 Harrison et al.
7,678,043 B2 3/2010 Gilad
7,689,437 B1 3/2010 Teller et al.
7,689,833 B2 3/2010 Lange
7,697,994 B2 4/2010 VanDanacker et al.
7,712,288 B2 5/2010 Ramasubramanian et al.
7,720,036 B2 5/2010 Sadri
7,729,776 B2 6/2010 Von Arx et al.
7,733,224 B2 6/2010 Tran
7,736,318 B2 6/2010 Costentino
7,747,454 B2 6/2010 Bartfeld et al.
7,756,587 B2 7/2010 Penner et al.
7,764,996 B2 7/2010 Zhang et al.
7,779,614 B1 8/2010 McGonagle et al.
7,796,043 B2 9/2010 Euliano et al.
7,797,033 B2 9/2010 D'Andrea et al.
7,806,852 B1 10/2010 Jursen
7,809,399 B2 10/2010 Lu
7,811,231 B2 10/2010 Jin et al.
7,844,341 B2 11/2010 Von Arx et al.
7,860,731 B2 12/2010 Jackson et al.
7,899,526 B2 3/2011 Benditt et al.
7,904,133 B2 3/2011 Gehman et al.
D639,437 S 6/2011 Bishay et al.
7,978,064 B2 7/2011 Zdeblick et al.
8,025,149 B2 9/2011 Sterry et al.
8,036,731 B2 10/2011 Kimchy et al.
8,060,249 B2 11/2011 Bear et al.
8,073,707 B2 12/2011 Teller et al.
8,083,128 B2 12/2011 Dembo et al.
8,123,576 B2 2/2012 Kim
8,135,596 B2 3/2012 Jung et al.
8,142,513 B2 3/2012 Shalon et al.
8,177,611 B2 5/2012 Kang
8,180,425 B2 5/2012 Selvitelli et al.
8,185,191 B1 5/2012 Shapiro et al.
8,185,646 B2 5/2012 Headley
8,200,320 B2 6/2012 Kovacs
8,209,018 B2 6/2012 Osorio et al.

(56) References Cited

U.S. PATENT DOCUMENTS

| | | | | |
|---|---|---|---|---|
| 8,214,007 | B2 | 7/2012 | Baker et al. | |
| 8,224,667 | B1 | 7/2012 | Miller et al. | |
| 8,238,998 | B2 | 8/2012 | Park | |
| 8,249,686 | B2 | 8/2012 | Libbus et al. | |
| 8,253,586 | B1 | 8/2012 | Matak | |
| 8,254,853 | B2 | 8/2012 | Rofougaran | |
| 8,258,962 | B2 | 9/2012 | Robertson et al. | |
| 8,262,394 | B2 | 9/2012 | Walker et al. | |
| 8,271,106 | B2 | 9/2012 | Wehba et al. | |
| 8,285,356 | B2 | 10/2012 | Bly et al. | |
| 8,290,574 | B2 | 10/2012 | Felid et al. | |
| 8,301,232 | B2 | 10/2012 | Albert et al. | |
| 8,308,640 | B2 | 11/2012 | Baldus et al. | |
| 8,314,619 | B2 | 11/2012 | Takiguchi | |
| 8,315,687 | B2 | 11/2012 | Cross et al. | |
| 8,343,068 | B2 | 1/2013 | Najafi et al. | |
| 8,369,936 | B2 | 2/2013 | Farringdon et al. | |
| 8,386,009 | B2 | 2/2013 | Lindberg et al. | |
| 8,389,003 | B2 | 3/2013 | Mintchev et al. | |
| 8,404,275 | B2 | 3/2013 | Habboushe | |
| 8,440,274 | B2 | 5/2013 | Wang | |
| 8,454,528 | B2 | 6/2013 | Yuen et al. | |
| 8,454,561 | B2 | 6/2013 | Uber, III et al. | |
| 8,514,086 | B2 | 8/2013 | Harper et al. | |
| 8,542,123 | B2 | 9/2013 | Robertson | |
| 8,564,432 | B2 | 10/2013 | Covannon et al. | |
| 8,564,627 | B2 | 10/2013 | Suzuki et al. | |
| 8,597,186 | B2 | 12/2013 | Hafezi et al. | |
| 8,634,838 | B2 | 1/2014 | Hellwig et al. | |
| 8,660,645 | B2 | 2/2014 | Stevenson et al. | |
| 8,668,280 | B2 | 3/2014 | Heller et al. | |
| 8,668,643 | B2 | 3/2014 | Kinast | |
| 8,709,635 | B1 * | 4/2014 | Benson .................. | H01M 6/04 428/188 |
| 8,718,193 | B2 | 5/2014 | Arne et al. | |
| 8,722,085 | B2 | 5/2014 | McKinney et al. | |
| 8,762,733 | B2 | 6/2014 | Derchak et al. | |
| 8,771,183 | B2 | 7/2014 | Sloan | |
| 8,810,260 | B1 | 8/2014 | Zhou | |
| 8,810,409 | B2 | 8/2014 | Robertson et al. | |
| 8,823,510 | B2 | 9/2014 | Downey et al. | |
| 8,836,513 | B2 | 9/2014 | Hafezi et al. | |
| 8,838,217 | B2 | 9/2014 | Myr | |
| 8,868,453 | B2 | 10/2014 | Zdeblick | |
| 8,908,943 | B2 | 12/2014 | Berry et al. | |
| 8,926,509 | B2 | 1/2015 | Magar et al. | |
| 8,932,221 | B2 | 1/2015 | Colliou et al. | |
| 8,945,005 | B2 | 2/2015 | Hafezi et al. | |
| 8,956,287 | B2 | 2/2015 | Zdeblick et al. | |
| 8,966,973 | B1 | 3/2015 | Milone | |
| 8,989,837 | B2 | 3/2015 | Weinstein et al. | |
| 9,031,658 | B2 | 5/2015 | Chiao et al. | |
| 9,047,746 | B1 | 6/2015 | Euliano et al. | |
| 9,060,708 | B2 | 6/2015 | Robertson et al. | |
| 9,088,168 | B2 | 7/2015 | Mach et al. | |
| 9,125,868 | B2 | 9/2015 | McKinney et al. | |
| 9,189,941 | B2 | 11/2015 | Eschelman et al. | |
| 9,226,663 | B2 | 1/2016 | Fei | |
| 9,226,679 | B2 | 1/2016 | Balda | |
| 9,235,683 | B2 | 1/2016 | Robertson et al. | |
| 9,258,035 | B2 | 2/2016 | Robertson et al. | |
| 9,270,025 | B2 | 2/2016 | Robertson et al. | |
| 9,277,864 | B2 | 3/2016 | Yang et al. | |
| 9,278,177 | B2 | 3/2016 | Edwards et al. | |
| 9,433,371 | B2 | 9/2016 | Hafezi et al. | |
| 9,439,582 | B2 | 9/2016 | Berkman et al. | |
| 9,439,599 | B2 | 9/2016 | Thompson et al. | |
| 9,444,503 | B2 | 9/2016 | Arne et al. | |
| 9,517,012 | B2 | 12/2016 | Lane et al. | |
| 9,603,550 | B2 | 3/2017 | Behzadi | |
| 9,883,819 | B2 | 2/2018 | Jensen et al. | |
| 2001/0027331 | A1 | 10/2001 | Thompson | |
| 2001/0031071 | A1 | 10/2001 | Nichols et al. | |
| 2001/0039503 | A1 | 11/2001 | Chan et al. | |
| 2001/0044588 | A1 | 11/2001 | Mault | |
| 2001/0051766 | A1 | 12/2001 | Gazdinski | |
| 2001/0056262 | A1 | 12/2001 | Cabiri et al. | |
| 2002/0002326 | A1 | 1/2002 | Causey et al. | |
| 2002/0019586 | A1 | 2/2002 | Teller et al. | |
| 2002/0026111 | A1 | 2/2002 | Ackerman | |
| 2002/0032384 | A1 | 3/2002 | Raymond et al. | |
| 2002/0032385 | A1 | 3/2002 | Raymond et al. | |
| 2002/0040278 | A1 | 4/2002 | Anuzis et al. | |
| 2002/0067270 | A1 | 6/2002 | Yarin et al. | |
| 2002/0077620 | A1 | 6/2002 | Sweeney et al. | |
| 2002/0128934 | A1 | 9/2002 | Shaer | |
| 2002/0132226 | A1 | 9/2002 | Nair | |
| 2002/0138009 | A1 | 9/2002 | Brockway et al. | |
| 2002/0184415 | A1 | 12/2002 | Naghavi et al. | |
| 2002/0192159 | A1 | 12/2002 | Reitberg | |
| 2002/0193669 | A1 | 12/2002 | Glukhovsky | |
| 2002/0193846 | A1 | 12/2002 | Pool et al. | |
| 2002/0198470 | A1 | 12/2002 | Imran et al. | |
| 2003/0017826 | A1 | 1/2003 | Fishman | |
| 2003/0023150 | A1 | 1/2003 | Yokoi et al. | |
| 2003/0028226 | A1 | 2/2003 | Thompson | |
| 2003/0037063 | A1 | 2/2003 | Schwartz | |
| 2003/0063522 | A1 | 4/2003 | Sagar | |
| 2003/0065536 | A1 | 4/2003 | Hansen | |
| 2003/0076179 | A1 | 4/2003 | Branch et al. | |
| 2003/0083559 | A1 | 5/2003 | Thompson | |
| 2003/0126593 | A1 | 7/2003 | Mault | |
| 2003/0130714 | A1 | 7/2003 | Nielsen et al. | |
| 2003/0135128 | A1 | 7/2003 | Suffin et al. | |
| 2003/0135392 | A1 | 7/2003 | Vrijens et al. | |
| 2003/0152622 | A1 | 8/2003 | Louie-Helm et al. | |
| 2003/0158466 | A1 | 8/2003 | Lynn et al. | |
| 2003/0158756 | A1 | 8/2003 | Abramson | |
| 2003/0162556 | A1 | 8/2003 | Libes | |
| 2003/0164401 | A1 | 9/2003 | Andreasson et al. | |
| 2003/0167000 | A1 | 9/2003 | Mullick et al. | |
| 2003/0171791 | A1 | 9/2003 | KenKnight | |
| 2003/0171898 | A1 | 9/2003 | Tarassenko et al. | |
| 2003/0181788 | A1 | 9/2003 | Yokoi et al. | |
| 2003/0181815 | A1 | 9/2003 | Ebner et al. | |
| 2003/0185286 | A1 | 10/2003 | Yuen | |
| 2003/0187337 | A1 | 10/2003 | Tarassenko et al. | |
| 2003/0187338 | A1 | 10/2003 | Say et al. | |
| 2003/0195403 | A1 | 10/2003 | Berner et al. | |
| 2003/0198619 | A1 | 10/2003 | Dong et al. | |
| 2003/0213495 | A1 | 11/2003 | Fujita et al. | |
| 2003/0214579 | A1 | 11/2003 | Iddan | |
| 2003/0216622 | A1 | 11/2003 | Meron et al. | |
| 2003/0216625 | A1 | 11/2003 | Phipps | |
| 2003/0216666 | A1 | 11/2003 | Ericson et al. | |
| 2003/0216729 | A1 | 11/2003 | Marchitto | |
| 2003/0216793 | A1 | 11/2003 | Karlsson et al. | |
| 2003/0229382 | A1 | 12/2003 | Sun et al. | |
| 2003/0232895 | A1 | 12/2003 | Omidian et al. | |
| 2004/0008123 | A1 | 1/2004 | Carrender et al. | |
| 2004/0018476 | A1 | 1/2004 | LaDue | |
| 2004/0019172 | A1 | 1/2004 | Yang et al. | |
| 2004/0034295 | A1 | 2/2004 | Salganicoff | |
| 2004/0049245 | A1 | 3/2004 | Gass | |
| 2004/0073095 | A1 | 4/2004 | Causey et al. | |
| 2004/0073454 | A1 | 4/2004 | Urquhart et al. | |
| 2004/0077995 | A1 | 4/2004 | Ferek-Petric | |
| 2004/0082982 | A1 | 4/2004 | Gord et al. | |
| 2004/0087839 | A1 | 5/2004 | Raymond et al. | |
| 2004/0092801 | A1 | 5/2004 | Drakulic | |
| 2004/0106859 | A1 | 6/2004 | Say et al. | |
| 2004/0111011 | A1 | 6/2004 | Uchiyama et al. | |
| 2004/0115507 | A1 | 6/2004 | Potter et al. | |
| 2004/0115517 | A1 | 6/2004 | Fukada et al. | |
| 2004/0121015 | A1 | 6/2004 | Chidlaw et al. | |
| 2004/0122296 | A1 | 6/2004 | Hatlestad | |
| 2004/0122297 | A1 | 6/2004 | Stahmann et al. | |
| 2004/0138558 | A1 | 7/2004 | Dunki-Jacobs et al. | |
| 2004/0147326 | A1 | 7/2004 | Stiles | |
| 2004/0148140 | A1 | 7/2004 | Tarassenko et al. | |
| 2004/0153007 | A1 | 8/2004 | Harris | |
| 2004/0167226 | A1 | 8/2004 | Serafini | |
| 2004/0167801 | A1 | 8/2004 | Say et al. | |
| 2004/0171914 | A1 | 9/2004 | Avni | |

(56) References Cited

U.S. PATENT DOCUMENTS

2004/0193020 A1 9/2004 Chiba
2004/0193029 A1 9/2004 Gluhovsky
2004/0193446 A1 9/2004 Mayer et al.
2004/0199222 A1 10/2004 Sun et al.
2004/0215084 A1 10/2004 Shimizu et al.
2004/0218683 A1 11/2004 Batra
2004/0220643 A1 11/2004 Schmidt
2004/0224644 A1 11/2004 Wu
2004/0225199 A1 11/2004 Evanyk
2004/0253304 A1 12/2004 Gross et al.
2004/0258571 A1 12/2004 Lee et al.
2004/0260154 A1 12/2004 Sidelnik
2004/0267240 A1 12/2004 Gross et al.
2005/0017841 A1 1/2005 Doi
2005/0020887 A1 1/2005 Goldberg
2005/0021103 A1 1/2005 DiLorenzo
2005/0021370 A1 1/2005 Riff
2005/0021372 A1 1/2005 Mikkelsen
2005/0024198 A1 2/2005 Ward
2005/0027175 A1 2/2005 Yang
2005/0027205 A1 2/2005 Tarassenko et al.
2005/0038321 A1 2/2005 Fujita et al.
2005/0038680 A1 2/2005 McMahon
2005/0043583 A1 2/2005 Killman et al.
2005/0043634 A1 2/2005 Yokoi et al.
2005/0043894 A1 2/2005 Fernandez
2005/0054897 A1 3/2005 Hashimoto et al.
2005/0055014 A1 3/2005 Coppeta et al.
2005/0062644 A1 3/2005 Leci
2005/0065407 A1 3/2005 Nakamura et al.
2005/0070778 A1 3/2005 Lackey
2005/0075145 A1 4/2005 Dvorak et al.
2005/0090753 A1 4/2005 Goor et al.
2005/0092108 A1 5/2005 Andermo
2005/0096514 A1 5/2005 Starkebaum
2005/0096562 A1 5/2005 Delalic et al.
2005/0101843 A1 5/2005 Quinn
2005/0101872 A1 5/2005 Sattler
2005/0115561 A1 6/2005 Stahmann et al.
2005/0116820 A1 6/2005 Goldreich
2005/0117389 A1 6/2005 Worledge
2005/0121322 A1 6/2005 Say et al.
2005/0131281 A1 6/2005 Ayer et al.
2005/0137480 A1 6/2005 Alt et al.
2005/0143623 A1 6/2005 Kojima
2005/0146594 A1 7/2005 Nakatani et al.
2005/0148883 A1 7/2005 Boesen
2005/0151625 A1 7/2005 Lai
2005/0154277 A1 7/2005 Tang et al.
2005/0154428 A1 7/2005 Bruinsma
2005/0156709 A1 7/2005 Gilbert et al.
2005/0159789 A1 7/2005 Brockway
2005/0165323 A1 7/2005 Montgomery
2005/0177069 A1 8/2005 Takizawa
2005/0182389 A1 8/2005 LaPorte
2005/0187789 A1 8/2005 Hatlestad et al.
2005/0192489 A1 9/2005 Marshall
2005/0197680 A1 9/2005 DelMain et al.
2005/0228268 A1 10/2005 Cole
2005/0234307 A1 10/2005 Heinonen
2005/0240305 A1 10/2005 Bogash et al.
2005/0245794 A1 11/2005 Dinsmoor
2005/0245839 A1 11/2005 Stivoric et al.
2005/0259768 A1 11/2005 Yang et al.
2005/0261559 A1 11/2005 Mumford
2005/0267550 A1 12/2005 Hess et al.
2005/0267556 A1 12/2005 Shuros et al.
2005/0267756 A1 12/2005 Schultz et al.
2005/0277912 A1 12/2005 John
2005/0277999 A1 12/2005 Strother et al.
2005/0280539 A1 12/2005 Pettus
2005/0285732 A1 12/2005 Sengupta et al.
2005/0285746 A1 12/2005 Sengupta
2005/0288594 A1 12/2005 Lewkowicz et al.
2006/0001496 A1 1/2006 Abrosimov et al.
2006/0028727 A1 2/2006 Moon et al.
2006/0036134 A1 2/2006 Tarassenko et al.
2006/0058602 A1 3/2006 Kwiatkowski et al.
2006/0061472 A1 3/2006 Lovoi et al.
2006/0065713 A1 3/2006 Kingery
2006/0068006 A1 3/2006 Begleiter
2006/0074283 A1 4/2006 Henderson
2006/0074319 A1 4/2006 Barnes et al.
2006/0078765 A1 4/2006 Yang et al.
2006/0089858 A1 4/2006 Ling
2006/0095091 A1 5/2006 Drew
2006/0095093 A1 5/2006 Bettesh et al.
2006/0100533 A1 5/2006 Han
2006/0107997 A1* 5/2006 Matsui .................. H01M 4/928
136/263
2006/0109058 A1 5/2006 Keating
2006/0110962 A1 5/2006 Powell
2006/0122474 A1 6/2006 Teller et al.
2006/0122667 A1 6/2006 Chavan et al.
2006/0127749 A1* 6/2006 Christie .................... B22F 3/11
429/121
2006/0129060 A1 6/2006 Lee et al.
2006/0136266 A1 6/2006 Tarassenko et al.
2006/0142648 A1 6/2006 Banet
2006/0145876 A1 7/2006 Kimura
2006/0148254 A1 7/2006 McLean
2006/0149339 A1 7/2006 Burnes
2006/0155174 A1 7/2006 Glukhovsky et al.
2006/0155183 A1 7/2006 Kroecker
2006/0158820 A1 7/2006 Takiguchi
2006/0161225 A1 7/2006 Sormann et al.
2006/0179949 A1 8/2006 Kim
2006/0183992 A1 8/2006 Kawashima
2006/0183993 A1 8/2006 Horn
2006/0184092 A1 8/2006 Atanasoska et al.
2006/0204738 A1 9/2006 Dubrow et al.
2006/0204764 A1 9/2006 Hirao et al.
2006/0210626 A1 9/2006 Spaeder
2006/0216603 A1 9/2006 Choi
2006/0218011 A1 9/2006 Walker
2006/0229053 A1 10/2006 Sivard
2006/0235489 A1 10/2006 Drew
2006/0243288 A1 11/2006 Kim et al.
2006/0247505 A1 11/2006 Siddiqui
2006/0253004 A1 11/2006 Frisch et al.
2006/0253005 A1 11/2006 Drinan
2006/0255064 A1 11/2006 Donaldson
2006/0265246 A1 11/2006 Hoag
2006/0267774 A1 11/2006 Feinberg et al.
2006/0270346 A1 11/2006 Ibrahim
2006/0273882 A1 12/2006 Posamentier
2006/0276702 A1 12/2006 McGinnis
2006/0280227 A1 12/2006 Pinkney
2006/0282001 A1 12/2006 Noel
2006/0285607 A1 12/2006 Strodtbeck et al.
2006/0287693 A1 12/2006 Kraft et al.
2006/0289640 A1 12/2006 Mercure
2006/0293607 A1 12/2006 Alt
2007/0000776 A1 1/2007 Karube et al.
2007/0002038 A1 1/2007 Suzuki
2007/0006636 A1 1/2007 King et al.
2007/0008113 A1 1/2007 Spoonhower et al.
2007/0016089 A1 1/2007 Fischell et al.
2007/0027386 A1 2/2007 Such
2007/0027388 A1 2/2007 Chou
2007/0038054 A1 2/2007 Zhou
2007/0049339 A1 3/2007 Barak et al.
2007/0055098 A1 3/2007 Shimizu et al.
2007/0060797 A1 3/2007 Ball
2007/0060800 A1 3/2007 Drinan et al.
2007/0066929 A1 3/2007 Ferren et al.
2007/0072156 A1 3/2007 Kaufman et al.
2007/0073353 A1 3/2007 Rooney et al.
2007/0088194 A1 4/2007 Tahar
2007/0096765 A1 5/2007 Kagan
2007/0106346 A1 5/2007 Bergelson
2007/0123772 A1* 5/2007 Euliano .................. A61B 5/073
600/407
2007/0129622 A1 6/2007 Bourget

(56) References Cited

U.S. PATENT DOCUMENTS

2007/0130287 A1 6/2007 Kumar
2007/0135691 A1 6/2007 Zingelewicz et al.
2007/0135803 A1 6/2007 Belson
2007/0141445 A1* 6/2007 Hertz .................. H01M 4/8621 429/482
2007/0142721 A1 6/2007 Berner et al.
2007/0156016 A1 7/2007 Betesh
2007/0160789 A1 7/2007 Merical
2007/0162089 A1 7/2007 Mosesov
2007/0162090 A1 7/2007 Penner
2007/0167495 A1 7/2007 Brown et al.
2007/0167848 A1 7/2007 Kuo et al.
2007/0172424 A1 7/2007 Roser
2007/0173701 A1 7/2007 Al-Ali
2007/0179347 A1 8/2007 Tarassenko et al.
2007/0179371 A1 8/2007 Peyser et al.
2007/0180047 A1 8/2007 Dong et al.
2007/0185393 A1 8/2007 Zhou
2007/0191002 A1 8/2007 Ge
2007/0196456 A1 8/2007 Stevens
2007/0207793 A1 9/2007 Myer
2007/0207858 A1 9/2007 Breving
2007/0208233 A1 9/2007 Kovacs
2007/0213659 A1 9/2007 Trovato et al.
2007/0237719 A1 10/2007 Jones
2007/0244370 A1 10/2007 Kuo et al.
2007/0244810 A1 10/2007 Rudolph
2007/0249946 A1 10/2007 Kumar et al.
2007/0255198 A1 11/2007 Leong et al.
2007/0255330 A1 11/2007 Lee
2007/0270672 A1 11/2007 Hayter
2007/0279217 A1 12/2007 Venkatraman
2007/0282174 A1 12/2007 Sabatino
2007/0282177 A1 12/2007 Pilz
2007/0291715 A1 12/2007 Laroia et al.
2007/0299480 A1 12/2007 Hill
2008/0004503 A1 1/2008 Nisani et al.
2008/0014866 A1 1/2008 Lipowshi
2008/0015421 A1 1/2008 Penner
2008/0015494 A1 1/2008 Santini et al.
2008/0015893 A1 1/2008 Miller et al.
2008/0020037 A1 1/2008 Robertson et al.
2008/0021519 A1 1/2008 DeGeest
2008/0021521 A1 1/2008 Shah
2008/0027679 A1 1/2008 Shklarski
2008/0033273 A1 2/2008 Zhou
2008/0033301 A1 2/2008 Dellavecchia et al.
2008/0038588 A1 2/2008 Lee
2008/0039700 A1 2/2008 Drinan et al.
2008/0045843 A1 2/2008 Tsuji et al.
2008/0046038 A1 2/2008 Hill
2008/0051647 A1 2/2008 Wu et al.
2008/0051667 A1 2/2008 Goldreich
2008/0051767 A1 2/2008 Rossing et al.
2008/0058614 A1 3/2008 Banet
2008/0062856 A1 3/2008 Feher
2008/0065168 A1 3/2008 Bitton et al.
2008/0074307 A1 3/2008 Boric-Lubecke
2008/0077015 A1 3/2008 Botic-Lubecke
2008/0077028 A1 3/2008 Schaldach et al.
2008/0077188 A1 3/2008 Denker et al.
2008/0077430 A1 3/2008 Singer et al.
2008/0091089 A1 4/2008 Guillory et al.
2008/0091114 A1 4/2008 Min
2008/0097549 A1 4/2008 Colbaugh
2008/0097917 A1 4/2008 Dicks
2008/0099366 A1 5/2008 Niemic et al.
2008/0103440 A1 5/2008 Ferren et al.
2008/0112885 A1 5/2008 Okunev et al.
2008/0114224 A1 5/2008 Bandy et al.
2008/0119705 A1 5/2008 Patel
2008/0119716 A1 5/2008 Boric-Lubecke
2008/0121825 A1 5/2008 Trovato et al.
2008/0137566 A1 6/2008 Marholev
2008/0139907 A1 6/2008 Rao et al.
2008/0140403 A1 6/2008 Hughes et al.
2008/0146871 A1 6/2008 Arneson et al.
2008/0146889 A1 6/2008 Young
2008/0146892 A1 6/2008 LeBeouf
2008/0154104 A1 6/2008 Lamego
2008/0166992 A1 7/2008 Ricordi
2008/0175898 A1 7/2008 Jones et al.
2008/0183245 A1 7/2008 Van Oort
2008/0188763 A1 8/2008 John et al.
2008/0188837 A1 8/2008 Belsky et al.
2008/0194912 A1 8/2008 Trovato et al.
2008/0208009 A1 8/2008 Shklarski
2008/0214901 A1 9/2008 Gehman
2008/0214903 A1 9/2008 Orbach
2008/0214985 A1 9/2008 Yanaki
2008/0223936 A1 9/2008 Mickle et al.
2008/0243020 A1 10/2008 Chou
2008/0249360 A1 10/2008 Li
2008/0262320 A1 10/2008 Schaefer et al.
2008/0262336 A1 10/2008 Ryu
2008/0269664 A1 10/2008 Trovato et al.
2008/0275312 A1 11/2008 Mosesov
2008/0281636 A1 11/2008 Jung et al.
2008/0284599 A1 11/2008 Zdeblick et al.
2008/0288026 A1 11/2008 Cross et al.
2008/0288027 A1 11/2008 Kroll
2008/0294020 A1 11/2008 Sapounas
2008/0299197 A1 12/2008 Toneguzzo et al.
2008/0300572 A1 12/2008 Rankers
2008/0303638 A1 12/2008 Nguyen
2008/0303665 A1 12/2008 Naik et al.
2008/0306357 A1 12/2008 Korman
2008/0306359 A1 12/2008 Zdeblick et al.
2008/0306360 A1 12/2008 Robertson et al.
2008/0311852 A1 12/2008 Hansen
2008/0312522 A1 12/2008 Rowlandson
2008/0316020 A1 12/2008 Robertson
2009/0006133 A1 1/2009 Weinert
2009/0009330 A1 1/2009 Sakama et al.
2009/0009332 A1 1/2009 Nunez et al.
2009/0024045 A1 1/2009 Prakash
2009/0024112 A1 1/2009 Edwards et al.
2009/0030293 A1 1/2009 Cooper et al.
2009/0030297 A1 1/2009 Miller
2009/0034209 A1 2/2009 Joo
2009/0043171 A1 2/2009 Rule
2009/0048498 A1 2/2009 Riskey
2009/0062634 A1 3/2009 Say et al.
2009/0062670 A1 3/2009 Sterling
2009/0062730 A1 3/2009 Woo
2009/0069642 A1 3/2009 Gao
2009/0069655 A1 3/2009 Say et al.
2009/0069656 A1 3/2009 Say et al.
2009/0069657 A1 3/2009 Say et al.
2009/0069658 A1 3/2009 Say et al.
2009/0076340 A1 3/2009 Libbus et al.
2009/0076343 A1 3/2009 James
2009/0076350 A1 3/2009 Bly et al.
2009/0076397 A1 3/2009 Libbus et al.
2009/0082645 A1 3/2009 Hafezi et al.
2009/0087483 A1 4/2009 Sison
2009/0088618 A1 4/2009 Arneson
2009/0099435 A1 4/2009 Say et al.
2009/0105561 A1 4/2009 Boydon et al.
2009/0110148 A1 4/2009 Zhang
2009/0112626 A1 4/2009 Talbot
2009/0124871 A1 5/2009 Arshak
2009/0131774 A1 5/2009 Sweitzer
2009/0134181 A1 5/2009 Wachman et al.
2009/0135886 A1 5/2009 Robertson et al.
2009/0142853 A1 6/2009 Warrington et al.
2009/0149708 A1 6/2009 Hyde et al.
2009/0149839 A1 6/2009 Hyde et al.
2009/0157113 A1 6/2009 Marcotte
2009/0157358 A1 6/2009 Kim
2009/0161602 A1 6/2009 Matsumoto
2009/0163789 A1 6/2009 Say et al.
2009/0171180 A1 7/2009 Pering
2009/0173628 A1 7/2009 Say et al.

(56) References Cited

U.S. PATENT DOCUMENTS

2009/0177055 A1 7/2009 Say et al.
2009/0177056 A1 7/2009 Say et al.
2009/0177057 A1 7/2009 Say et al.
2009/0177058 A1 7/2009 Say et al.
2009/0177059 A1 7/2009 Say et al.
2009/0177060 A1 7/2009 Say et al.
2009/0177061 A1 7/2009 Say et al.
2009/0177062 A1 7/2009 Say et al.
2009/0177063 A1 7/2009 Say et al.
2009/0177064 A1 7/2009 Say et al.
2009/0177065 A1 7/2009 Say et al.
2009/0177066 A1 7/2009 Say et al.
2009/0182206 A1 7/2009 Najafi
2009/0182207 A1 7/2009 Riskey et al.
2009/0182212 A1 7/2009 Say et al.
2009/0182213 A1 7/2009 Say et al.
2009/0182214 A1 7/2009 Say et al.
2009/0182215 A1 7/2009 Say et al.
2009/0182388 A1 7/2009 Von Arx
2009/0187088 A1 7/2009 Say et al.
2009/0187089 A1 7/2009 Say et al.
2009/0187090 A1 7/2009 Say et al.
2009/0187091 A1 7/2009 Say et al.
2009/0187092 A1 7/2009 Say et al.
2009/0187093 A1 7/2009 Say et al.
2009/0187094 A1 7/2009 Say et al.
2009/0187095 A1 7/2009 Say et al.
2009/0187381 A1 7/2009 King et al.
2009/0192351 A1 7/2009 Nishino
2009/0192368 A1 7/2009 Say et al.
2009/0192369 A1 7/2009 Say et al.
2009/0192370 A1 7/2009 Say et al.
2009/0192371 A1 7/2009 Say et al.
2009/0192372 A1 7/2009 Say et al.
2009/0192373 A1 7/2009 Say et al.
2009/0192374 A1 7/2009 Say et al.
2009/0192375 A1 7/2009 Say et al.
2009/0192376 A1 7/2009 Say et al.
2009/0192377 A1 7/2009 Say et al.
2009/0192378 A1 7/2009 Say et al.
2009/0192379 A1 7/2009 Say et al.
2009/0198115 A1 8/2009 Say et al.
2009/0198116 A1 8/2009 Say et al.
2009/0198175 A1 8/2009 Say et al.
2009/0203964 A1 8/2009 Shimizu et al.
2009/0203971 A1 8/2009 Sciarappa
2009/0203972 A1 8/2009 Heneghan
2009/0203978 A1 8/2009 Say et al.
2009/0204265 A1 8/2009 Hackett
2009/0210164 A1 8/2009 Say et al.
2009/0216101 A1 8/2009 Say et al.
2009/0216102 A1 8/2009 Say et al.
2009/0227204 A1 9/2009 Robertson et al.
2009/0227876 A1 9/2009 Tran
2009/0227940 A1 9/2009 Say et al.
2009/0227941 A1 9/2009 Say et al.
2009/0227988 A1 9/2009 Wood et al.
2009/0228214 A1 9/2009 Say et al.
2009/0231125 A1 9/2009 Baldus
2009/0234200 A1 9/2009 Husheer
2009/0243833 A1 10/2009 Huang
2009/0247836 A1 10/2009 Cole et al.
2009/0253960 A1 10/2009 Takenaka et al.
2009/0256702 A1 10/2009 Robertson
2009/0264714 A1 10/2009 Chou
2009/0264964 A1 10/2009 Abrahamson
2009/0265186 A1 10/2009 Tarassenko et al.
2009/0273467 A1 11/2009 Elixmann
2009/0277815 A1 11/2009 Kohl et al.
2009/0281539 A1 11/2009 Selig
2009/0287109 A1 11/2009 Ferren et al.
2009/0292194 A1 11/2009 Libbus et al.
2009/0295548 A1 12/2009 Ronkka
2009/0296677 A1 12/2009 Mahany
2009/0301925 A1 12/2009 Alloro et al.
2009/0303920 A1 12/2009 Mahany
2009/0306633 A1 12/2009 Trovato et al.
2009/0312619 A1 12/2009 Say et al.
2009/0318303 A1 12/2009 Delamarche et al.
2009/0318761 A1 12/2009 Rabinovitz
2009/0318779 A1 12/2009 Tran
2009/0318783 A1 12/2009 Rohde
2009/0318793 A1 12/2009 Datta
2010/0001841 A1 1/2010 Cardullo
2010/0006585 A1 1/2010 Flowers et al.
2010/0010330 A1 1/2010 Rankers
2010/0015584 A1 1/2010 Singer et al.
2010/0033324 A1 2/2010 Shimizu et al.
2010/0036269 A1 2/2010 Ferren et al.
2010/0049004 A1 2/2010 Edman et al.
2010/0049006 A1 2/2010 Magar
2010/0049012 A1 2/2010 Dijksman et al.
2010/0049069 A1 2/2010 Tarassenko et al.
2010/0056878 A1 3/2010 Partin
2010/0056891 A1 3/2010 Say et al.
2010/0056939 A1 3/2010 Tarassenko et al.
2010/0057041 A1 3/2010 Hayter
2010/0062709 A1 3/2010 Kato
2010/0063438 A1 3/2010 Bengtsson
2010/0063841 A1 3/2010 D'Ambrosia et al.
2010/0069002 A1 3/2010 Rong
2010/0069717 A1 3/2010 Hafezi et al.
2010/0082367 A1 4/2010 Hains et al.
2010/0099967 A1 4/2010 Say et al.
2010/0099968 A1 4/2010 Say et al.
2010/0099969 A1 4/2010 Say et al.
2010/0100077 A1 4/2010 Rush
2010/0100078 A1 4/2010 Say et al.
2010/0100237 A1 4/2010 Ratnakar
2010/0106001 A1 4/2010 Say et al.
2010/0118853 A1 5/2010 Godfrey
2010/0131434 A1 5/2010 Magent et al.
2010/0139672 A1 6/2010 Kroll et al.
2010/0160742 A1 6/2010 Seidl et al.
2010/0168659 A1 7/2010 Say et al.
2010/0179398 A1 7/2010 Say et al.
2010/0183199 A1 7/2010 Smith et al.
2010/0185055 A1 7/2010 Robertson et al.
2010/0191073 A1 7/2010 Tarassenko et al.
2010/0203394 A1 8/2010 Bae et al.
2010/0210299 A1 8/2010 Gorbachov
2010/0217100 A1 8/2010 LeBoeuf et al.
2010/0222652 A1 9/2010 Cho
2010/0228113 A1 9/2010 Solosko
2010/0233026 A1 9/2010 Ismagliov et al.
2010/0234706 A1 9/2010 Gilland
2010/0234715 A1 9/2010 Shin
2010/0234914 A1 9/2010 Shen
2010/0245091 A1 9/2010 Singh
2010/0249541 A1 9/2010 Geva et al.
2010/0249881 A1 9/2010 Corndorf
2010/0256461 A1 10/2010 Mohamedali
2010/0259543 A1 10/2010 Tarassenko et al.
2010/0268048 A1 10/2010 Say et al.
2010/0268049 A1 10/2010 Say et al.
2010/0268050 A1 10/2010 Say et al.
2010/0268288 A1 10/2010 Hunter et al.
2010/0274111 A1 10/2010 Say et al.
2010/0280345 A1 11/2010 Say et al.
2010/0280346 A1 11/2010 Say et al.
2010/0295694 A1 11/2010 Kauffman et al.
2010/0298668 A1 11/2010 Hafezi et al.
2010/0298730 A1 11/2010 Tarassenko et al.
2010/0299155 A1 11/2010 Findlay et al.
2010/0312188 A1 12/2010 Robertson et al.
2010/0312577 A1 12/2010 Goodnow et al.
2010/0312580 A1 12/2010 Tarassenko et al.
2010/0332443 A1 12/2010 Gartenberg
2011/0004079 A1 1/2011 Al Ali et al.
2011/0009715 A1 1/2011 O'Reilly et al.
2011/0021983 A1 1/2011 Jurson
2011/0029622 A1 2/2011 Walker et al.
2011/0040203 A1 2/2011 Savage et al.
2011/0050431 A1 3/2011 Hood et al.

(56) References Cited

U.S. PATENT DOCUMENTS

| | | | |
|---|---|---|---|
| 2011/0054265 | A1 | 3/2011 | Hafezi et al. |
| 2011/0065983 | A1 | 3/2011 | Hafezi et al. |
| 2011/0077660 | A1 | 3/2011 | Janik et al. |
| 2011/0081860 | A1 | 4/2011 | Brown et al. |
| 2011/0105864 | A1 | 5/2011 | Robertson et al. |
| 2011/0112686 | A1 | 5/2011 | Nolan et al. |
| 2011/0124983 | A1 | 5/2011 | Kroll et al. |
| 2011/0144470 | A1 | 6/2011 | Mazar et al. |
| 2011/0160549 | A1 | 6/2011 | Saroka et al. |
| 2011/0212782 | A1 | 9/2011 | Thompson et al. |
| 2011/0224912 | A1 | 9/2011 | Bhavaraju et al. |
| 2011/0230732 | A1 | 9/2011 | Edman et al. |
| 2011/0237924 | A1 | 9/2011 | McGusty et al. |
| 2011/0270112 | A1 | 11/2011 | Manera et al. |
| 2011/0270135 | A1 | 11/2011 | Dooley et al. |
| 2011/0279963 | A1 | 11/2011 | Kumar et al. |
| 2012/0024889 | A1 | 2/2012 | Robertson et al. |
| 2012/0029309 | A1 | 2/2012 | Paquet et al. |
| 2012/0032816 | A1 | 2/2012 | Cho et al. |
| 2012/0062371 | A1 | 3/2012 | Radivojevic et al. |
| 2012/0071743 | A1 | 3/2012 | Todorov et al. |
| 2012/0083715 | A1 | 4/2012 | Yuen et al. |
| 2012/0089000 | A1 | 4/2012 | Bishay et al. |
| 2012/0101396 | A1 | 4/2012 | Solosko et al. |
| 2012/0116184 | A1 | 5/2012 | Shieh |
| 2012/0179004 | A1 | 7/2012 | Roesicke et al. |
| 2012/0197144 | A1 | 8/2012 | Christ et al. |
| 2012/0214140 | A1 | 8/2012 | Brynelson et al. |
| 2012/0265544 | A1 | 10/2012 | Hwang et al. |
| 2012/0299723 | A1 | 11/2012 | Hafezi et al. |
| 2012/0310070 | A1 | 12/2012 | Kumar et al. |
| 2012/0316413 | A1 | 12/2012 | Liu et al. |
| 2013/0002423 | A1 | 1/2013 | Robertson et al. |
| 2013/0030259 | A1 | 1/2013 | Thomsen et al. |
| 2013/0057385 | A1 | 3/2013 | Murakami et al. |
| 2013/0060115 | A1 | 3/2013 | Gehman et al. |
| 2013/0073312 | A1 | 3/2013 | Thompson et al. |
| 2013/0171596 | A1 | 7/2013 | French |
| 2013/0185228 | A1 | 7/2013 | Dresner |
| 2013/0196012 | A1 | 8/2013 | Dill |
| 2013/0275296 | A1 | 10/2013 | Tietzen et al. |
| 2013/0328416 | A1 | 12/2013 | Whitworth et al. |
| 2013/0338452 | A1 | 12/2013 | Robertson et al. |
| 2014/0004492 | A1 | 1/2014 | O'Reilly et al. |
| 2014/0039445 | A1 | 2/2014 | Austin et al. |
| 2014/0051965 | A1 | 2/2014 | Zdeblick et al. |
| 2014/0203950 | A1 | 7/2014 | Zdeblick et al. |
| 2014/0280125 | A1 | 9/2014 | Bhardwaj et al. |
| 2014/0308930 | A1 | 10/2014 | Tran |
| 2014/0315170 | A1 | 10/2014 | Ionescu et al. |
| 2014/0334575 | A1 | 11/2014 | Arne et al. |
| 2014/0349256 | A1 | 11/2014 | Connor |
| 2014/0374276 | A1 | 12/2014 | Guthrie et al. |
| 2015/0051465 | A1 | 2/2015 | Robertson et al. |
| 2015/0080677 | A1 | 3/2015 | Thompson et al. |
| 2015/0080678 | A1 | 3/2015 | Frank et al. |
| 2015/0080679 | A1 | 3/2015 | Frank et al. |
| 2015/0080680 | A1 | 3/2015 | Zdeblick et al. |
| 2015/0080681 | A1 | 3/2015 | Hafezi et al. |
| 2015/0127737 | A1 | 5/2015 | Thompson et al. |
| 2015/0127738 | A1 | 5/2015 | Thompson et al. |
| 2015/0149375 | A1 | 5/2015 | Thompson et al. |
| 2015/0165313 | A1 | 6/2015 | Thompson et al. |
| 2015/0171924 | A1 | 6/2015 | Zdeblick |
| 2016/0106339 | A1 | 4/2016 | Behzadi et al. |
| 2016/0155316 | A1 | 6/2016 | Hafezi et al. |
| 2017/0000180 | A1 | 1/2017 | Arne et al. |
| 2017/0215761 | A1 | 8/2017 | Zdeblick |
| 2017/0270779 | A1 | 9/2017 | Zdeblick et al. |
| 2017/0290513 | A1 | 10/2017 | O'Reilly et al. |
| 2017/0303818 | A1 | 10/2017 | Behzadi et al. |
| 2018/0026680 | A1 | 1/2018 | Shirvani et al. |
| 2018/0184698 | A1 | 7/2018 | Arne et al. |
| 2018/0279910 | A1 | 10/2018 | Jensen et al. |

FOREIGN PATENT DOCUMENTS

| | | |
|---|---|---|
| CN | 1991868 | 7/2007 |
| CN | 101005470 | 7/2007 |
| CN | 201076456 | 6/2008 |
| CN | 101524267 | 9/2009 |
| DE | 10313005 | 10/2004 |
| EP | 0344939 | 12/1989 |
| EP | 0526166 | 2/1993 |
| EP | 1199670 | 4/2002 |
| EP | 1246356 | 10/2002 |
| EP | 1342447 | 9/2003 |
| EP | 1534054 | 5/2005 |
| EP | 1702553 | 9/2006 |
| EP | 1098591 | 1/2007 |
| EP | 1789128 | 5/2007 |
| EP | 2143369 | 1/2010 |
| GB | 775071 | 5/1957 |
| GB | 2432862 | 6/2007 |
| IL | 172917 | 6/2010 |
| JP | 2000-506410 | 5/1912 |
| JP | 6117949 | 1/1986 |
| JP | S63280393 | 11/1988 |
| JP | H01285247 | 11/1989 |
| JP | 05-228128 | 9/1993 |
| JP | H0884779 | 4/1996 |
| JP | 09-330159 | 12/1997 |
| JP | 10-14898 | 1/1998 |
| JP | H11195415 | 7/1999 |
| JP | 2001078974 | 3/2001 |
| JP | 2002-224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003210395 | 7/2003 |
| JP | 3454525 | 10/2003 |
| JP | 2003325440 | 11/2003 |
| JP | 2004-7187 | 1/2004 |
| JP | 2004507188 | 3/2004 |
| JP | 2004-134384 | 4/2004 |
| JP | 2004274452 | 9/2004 |
| JP | 2004-313242 | 11/2004 |
| JP | 2004318534 | 11/2004 |
| JP | 2004364016 | 12/2004 |
| JP | 2005031840 | 2/2005 |
| JP | 2005-073886 | 3/2005 |
| JP | 2005-087552 | 4/2005 |
| JP | 2005-304880 | 4/2005 |
| JP | 2005124708 | 5/2005 |
| JP | 2005148021 | 6/2005 |
| JP | 2005152037 | 6/2005 |
| JP | 2005287691 | 10/2005 |
| JP | 2005-532841 | 11/2005 |
| JP | 2005-532849 | 11/2005 |
| JP | 2005343515 | 12/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 3876573 | 1/2007 |
| JP | 2007-159631 | 6/2007 |
| JP | 2007151809 | 6/2007 |
| JP | 2007200739 | 8/2007 |
| JP | 2007-313340 | 12/2007 |
| JP | 2007-330677 | 12/2007 |
| JP | 2008011865 | 1/2008 |
| JP | 2008501415 | 1/2008 |
| JP | 2008176434 | 7/2008 |
| JP | 2008191955 | 8/2008 |
| JP | 2008289724 | 12/2008 |
| JP | 2009034345 | 2/2009 |
| JP | 2009-061236 | 3/2009 |
| JP | 2009050541 | 3/2009 |
| JP | 2009065726 | 3/2009 |
| JP | 2011015817 | 1/2011 |
| JP | 2011519583 | 7/2011 |

(56) References Cited

FOREIGN PATENT DOCUMENTS

| | | |
|---|---|---|
| KR | 20020015907 | 3/2002 |
| KR | 20020061744 | 7/2002 |
| KR | 200600977523 | 7/2006 |
| KR | 927471 | 11/2009 |
| KR | 20110137001 | 12/2011 |
| KR | 10-2012-09995 | 9/2012 |
| TW | 200301864 | 7/2003 |
| TW | 553735 | 9/2003 |
| TW | 200724094 | 7/2007 |
| TW | 200812556 | 3/2008 |
| TW | 201120673 | 6/2011 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO9516393 | 6/1995 |
| WO | WO1997014112 | 4/1997 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000033246 | 6/2000 |
| WO | WO2001000085 | 1/2001 |
| WO | WO2001047466 | 7/2001 |
| WO | WO2001049364 | 7/2001 |
| WO | WO2001074011 | 10/2001 |
| WO | WO2001080731 | 11/2001 |
| WO | WO0235997 | 5/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005069887 | 8/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006016370 | 2/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO2006109072 | 10/2006 |
| WO | WO2006/123346 | 11/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007123923 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009032381 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010107980 | 9/2010 |
| WO | WO2010115194 | 10/2010 |
| WO | WO2010132331 | 11/2010 |
| WO | WO2010135516 | 11/2010 |
| WO | WO2011024560 | 3/2011 |

(56) References Cited

FOREIGN PATENT DOCUMENTS

| | | |
|---|---|---|
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |
| WO | WO2015112603 | 7/2015 |

OTHER PUBLICATIONS

Kang, H-K; et al.; "Tungsten/copper composite deposits produces by a cold spray"; Scripta Materialia 49 (2003) 1169-1174 (Year: 2003).*
Guimard, N., Sessler, J., & Schmidt, C. (2006). Design of a Novel Electrically Conducting Biocompatible Polymer with Degradable Linkages for Biomedical Applications. MRS Proceedings, 950, 0950-D09-08. (Year: 2006).*
Rivers, T., Hudson, T. and Schmidt, C. (2002), Synthesis of a Novel, Biodegradable Electrically Conducting Polymer for Biomedical Applications. Adv. Funct. Mater., 12: 33-37. (Year: 2002).*
Martins, J. I, et al; "Polypyrrole coatings as a treatment for zinc-coated steel surfaces against corrosion"; Corrosion Science, vol. 46, Issue 10, 2004, pp. 2361-2381. (Year: 2004).*
Ferguson et al., "Wireless communication with implanted medical devices using the conductive properties of the body," Expert Rev Med Devices, Jul. 2011, 8(4): 427-433.
Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.
Sharma, et al., "The Future is Wireless: Advances in Wireless Diagnostic and Therapeutic Technologies in Gastoenterology," Gastroenterology, Elesevier, Philadelphia, PA, vol. 137, No. 2, Aug. 1, 2009, pp. 434-439.
AADE, "AADE 37th Annual Meeting San Antonio Aug. 4-7, 2010" American Association of Diabetes Educators Aug. 2010; http://www.diabeteseducator.org/annualmeeting/2010/index.html; 2 pp.
Arshak et al., A Review and Adaptation of Methods of Object Tracking to Telemetry Capsules IC-Med; Jan. 2007 vol. 1, No. 1, Issue 1, 12pp.
"ASGE Technology Status Evaluation Report: wireless capsule endoscopy" American Soc. for Gastrointestinal Endoscopy; Apr. 2006 vol. 63, No. 4; 7 pp.
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Bohidar et al., "Dielectric Behavior of Gelatin Solutions and Gels" Colloid Polym Sci (1998) 276:81-86.
Carlson et al., "Evaluation of a non-invasive respiratory monitoring system for sleeping subjects" Physiological Measurement (1999) 20(1): 53.
Coury, L. "Conductance Measurement Part 1: Theory"; Current Separations, 18:3 (1999) p. 91-96.
Delvaux et al., "Capsule endoscopy: Technique and indications" Clinical Gastoenterology; Oct. 2008 vol. 22, Issue 5, 1pp. (Abstract Only).
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Evanczuk, S., "PIC MCU software library uses human body for secure communications link"; EDN Network; edn.com; Retrieved from internet Jun. 19, 2013 at http://www.edn.com/electronics-products/other/4407842/PIC-MCU-software-library-uses-human-body-for-secure-communications-link; Feb. 26, 2013; 5 pp.
Ferguson et al., "Dialectic Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gaglani S. "Put Your Phone, or Skin, on Vibrate" MedGadget; Mar. 2012 http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng; Dec. 2007 54(12) 1pp. (Abstract Only).
Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.
Halthion Medical Technologies "Providing Ambulatory Medical Devices Which Monitor, Measure and Record" webpage. Online website: http://www.halthion.com/; downloaded May 30, 2012; 2 pp.
Heydari et al., "Analysis of the PLL jitter due to power/ground and substrate noise"; IEEE Transactions on Circuits and Systems (2004) 51(12): 2404-16.
Hoeksma, J. "New 'smart pill' to track adherence" E-Health-Insider; http://www.e-health-insider.com/news/5910/new_'smart_pill'_monitors_medicines; May 17, 2010 (2010); 1pp.
Hoover et al., "Rx for health: Engineers design pill that signals it has been swallowed" University of Florida News; Mar. 2010 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
ISFET—Ion Sensitive Field-Effect Transistor; Microsens S.A. pdf document. First in Office Action dated Jun. 13, 2011 for U.S. Appl. No. 12/238,345; 4pp.
Intromedic, MicroCam Innovative Capsule Endoscope Pamphlet. (2006) 8 pp (http://www.intromedic.com/en/product/productinfo.asp).
Jimbo et al., "Gastric-fluid-utilized micro battery for micro medical devices" The Sixth International Workshop on Micro and Nanotechnology for Power Geneartion and Energy Conservation Applications, (2006) pp. 97-100.
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" Jun. 2010; http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Li, P-Y, et al. "An electrochemical intraocular drug delivery device", Sensors and Actuators A 143; p. 41-48.; Jul. 2007.
Lifescan, "OneTouch UltraLink™" http://www.lifescan.com/products/meters/ultralink; Jul. 2010 2 pp.
Lin et al., "Do Physiological Data Relate to Traditional Usability Indexes?" Proceedings of OZCHI 2005, Canberra, Australia (2005) 10 pp.
MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

(56) References Cited

OTHER PUBLICATIONS

MacKay et al., "Endoradiosonde" Nature, (1957) 1239-1240, 179 Nature Publishing Group.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-6/04/0004; 2 pp.
Medtronic, "CareLink Therapy Management Software for Diabetes" Jul. 2010; https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" Aug. 2010 http://www.medtronicdiabetes.com/products/index.html; 2 pp.
Medtronic, "Mini Med Paradigm® Revel™ Insulin Pump" Jul. 2010 http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Mini Mitter Co, Inc. 510(k) Premarket Notification Mini-Logger for Diagnostic Spirometer. Sep. 21, 1999.
Mojaverian et al., "Estimation of gastric residence time of the Heidelberg capsule in humans: effect of varying food composition" Gastroenterology (1985) 89:(2): 392-7.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Owano, N., "Study proposes smart sutures with sensors for wounds" phys.org. Aug. 2012. http://phys.org/news/2012-08-smart-sutures-sensors-wounds.html; 2pp.
"PALO Bluetooth Baseband" PALO Bluetooth Resource Center; Retrieved from internet Dec. 12, 2012 at URL:http://palowireless.com/bluearticles/baseband.asp; first cited in Office Action dated Jan. 17, 2013 for EP08853901.0 (2013); 6pp.
Park, "Medtronic to Buy MiniMed for $3.7 Billion" (2001) HomeCare; http://homecaremag.com/mag/medical_medtronic_buy_minimed/; 2 pp.
Platt, D., "Modulation and Deviation" AE6EO, Foothills Amateur Radio Society; Oct. 26, 2007; 61 pp.
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
Shawgo, R.S. et al. "BioMEMS from drug delivery", Current Opinion in Solid State and Material Science 6; May 2002, p. 329-334.
Shin et al., "A Simple Route to Metal Nanodots and Nanoporous Metal Films"; Nano Letters, vol. 2, No. 9 (2002) pp. 933-936.
"Smartlife awarded patent for knitted transducer" Innovation in Textiles News: http://www.innovationintextiles.com/articles/208.php; 2pp. Aug. 2009.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Trutag, Technologies, Inc., Spectral Microtags for Authentication and Anti-Counterfeiting; "Product Authentication and Brand Protection Solutions"; http://www.trutags.com/; downloaded Feb. 12, 2013 (2013); 1 pp.
Watson, et al., "Determination of the relationship between the pH and conductivity of gastric juice" Physiol Meas. 17 (1996) pp. 21-27.
Winter, J. et al. "The material properties of gelatin gels"; USA Ballistic Research Laboratories, Mar. 1975, p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sept. 3, 2006.
Zimmerman, "Personal Area Networks: Near-field intrabody communication" IBM Systems Journal (1996) 35 (3-4):609-17.
Aronson, J., "Meyer's Side Effects of Cardiovascular Drugs," Elsevier, Mar. 2, 2009, Medical , 840 pages. (Not Attached).
Au-Yeung, K., et al., "A Networked System for Self-Management of Drug Therapy and Wellness", Wireless Health '10, Oct. 5-7, 2010, San Diego, 9 pages.
Chan, Adrian D.C., et al.,; "Wavelet Distance Measure for Person Identification Using Electrocardiograms," IEEE Transactions on Instrumentation and Measurement, IEEE Service Center, Piscataway, NJ, US, vol. 57, No. 2, Feb. 1, 2008, pp. 248-253.
Herbig, S.M., "Asymmetric-membrane tablet coatings for osmotic drug delivery", Journal of Controlled Release 35 (1995) 127-136.
Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
McDermott-Wells, P., "What is Bluetooth?", IEEE Potentials, IEEE, New York, NY, vol. 23, No. 5, Dec. 1, 2004, pp. 33-35.
Sammoura, F. et al., "Water-activated disposable and long shelf life microbatteries", Sensors and Actuators A 111 (2004) 79-86.
VonStetten, F. et al., "Biofuel cells as power generation for implantable devices", Pore. Eurosensors XX, (2006), pp. 22-225.
Aydin et al., "Design and implementation considerations for an advanced wireless interface in miniaturized integrated sensor Microsystems" Sch. of Eng. & Electron., Edinburgh Univ., UK; Sep. 2003; Abstract Only (1 page).
Barrie, Heidelberg pH capsule gastric analysis. Texbook of Natural Medicine, (1992), Pizzorno, Murray & Barrie (4 pages).
Brock, "Smart Medicine: The Application of Auto-ID Technology to Healthcare" Auto-ID Labs (2002) http://www.autoidlabs.org/uploads/media/MIT-AUTOID-WH-010.pdf (14 pages).
Fawaz et al., "Enhanced Telemetry System using CP-QPSK Band-Pass Modulation Technique Suitable for Smart Pill Medical Application" IFIP IEEE Dubai Conference Apr. 2008; http://www.asic.fh-offenburg.de/downloads/ePille/IFIP_IEEE_Dubai_Conference.pdf (5 pages).
Greene, "Medicaid Efforts to Incentivize Healthy Behaviours", Center for Health Care Strategies, Inc., Resource Paper, Jul. 2007 (20 pages).

(56) References Cited

OTHER PUBLICATIONS

McKenzie et al., "Validation of a new telemetric core temperature monitor" J. Therm. Biol. (2004) 29(7-8):605-11 (4 pages).
Melanson, "Walkers swallow RFID pills for science" Engadget; Jul. 2008; http://www.engadget.com/2008/07/29/walkers-swallow-rfid-pills-for-science/ (1 page).
Minimitter Co. Inc. "Actiheart" Traditional 510(k) Summary. Sep. 27, 2005 (8 pages).
Minimitter Co. Inc. Noninvasive technology to help your studies succeed. Mini Mitter.com Mar. 31, 2009 (4 pages).
Mini Mitter Co, Inc. 510(k) Premarket Notification for VitalSense. Apr. 22, 2004 (11 pages).
Minimitter Co. Inc. VitalSense Integrated Physiological Monitoring System. Product Description. Jul. 2005 (4 pages).
Minimitter Co. Inc. VitalSense Wireless Vital Signs Monitoring. Temperatures.com Mar. 31, 2009 (3 pages).
"RFID "pill" monitors marchers" RFID News; Jul. 2008 http://www.rfidnews.org/2008/07/23/rfid-pill-monitors-marchers/ (4 pages).
"SensiVida minimally invasive clinical systems" Investor Presentation Oct. 2009 28pp; http://www.sensividamedtech.com/SensiVidaGeneralOctober09.pdf, pp. 1-28.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010), pp. 11-12.
"The SmartPill Wireless Motility Capsule" Smartpill, The Measure of GI Health; May 2010 http://www.smartpillcorp.com/index.cfm?pagepath=Products/The_SmartPill_Capsule&id=17814, (1 page).
Tatbul et al., "Confidence-based data management for personal area sensor networks" ACM International Conference Proceeding Series (2004) 72, (3 pages).
Walkey, "MOSFET Structure and Processing"; 97.398 Physical Electronics Lecture 20 (24 pages).
Zworkin, "A Radio Pill" Nature, (1957) 898, 179 Nature Publishing Group (1 page).
Description of ePatch Technology Platform for ECG and EMG, located it http://www.madebydelta.com/imported/images/DELTA_Web/documents/ME/ePatch_ECG_EMG.pdf, Dated Sep. 2, 2010 (1 page).
Browne, S.H., et al., "Let visuals tell the story: Medication adherence in patients with type II diabetes captured by a novel ingestion sensor platform," JMIR Mhealth Uhealth; 3(4): e108; 2015; 27 pages.
Frias, J. et al., "Effectiveness of Digital Medicines to Improve Clinical Outcomes in Patients with Uncontrolled Hypertension and Type 2 Diabetes: Prospective, Open-Label, Cluster-Randomized Pilot Clinical Trial," J Med Internet Res, 2017;19(7):e246; p. 15 (16 pages).
Noble et al., "Medication adherence and activity patterns underlying uncontrolled hypertension: Assessment and recommendations by practicing pharmacists using digital health care," JAPHA; 56 (2016) pp. 310-315 (6 pages).
Savage, G., "Predictive Analytics: Advancing Precision and Population Medicine," Harvard Health Policy Review, 2015; vol. 14; Issue 2; 4 pages.

* cited by examiner

IN-BODY POWER SOURCE HAVING HIGH SURFACE AREA ELECTRODE

CROSS-REFERENCE TO RELATED APPLICATIONS

This application is a continuation of U.S. patent application Ser. No. 12/527,190, filed Aug. 13, 2009, entitled IN-BODY POWER SOURCE HAVING HIGH SURFACE AREA ELECTRODE, which application is a 371 application of International Patent Application No. PCT/US2008/053999, filed Feb. 14, 2008, which application pursuant to 35 U.S.C. §119 (e), claims priority to the filing date of U.S. Provisional Patent Application No. 60/889,870 filed on Feb. 14, 2007; the disclosures of which are herein incorporated by reference.

INTRODUCTION

As medical technology advances, many diagnostic and therapeutic activities are carried out with increasingly small implantable medical or ingestible medical devices. Implantable and ingestible medical devices can be configured to perform a variety of different functions, including but not limited to: diagnostic functions, e.g., where the devices include one or more sensors; therapeutic functions, e.g., where the devices enable therapeutic action, such as delivery of electrical pulse, delivery of a pharmaceutically active agent; etc.

With implantable and ingestible medical and related technologies, there is always a desire to make the devices smaller, e.g., to provide for increased ease of use, etc. To decrease size, individual components of the devices must be designed with a reduced overall physical size, and yet maintain functionality.

One type of component that is present in many implantable and ingestible devices is a power source, e.g., batteries, capacitors, etc. There is continued interest in the development of smaller and smaller power sources that nonetheless have adequate and reliable functionality such that they can be employed with in-body devices, such as implantable and ingestible devices.

SUMMARY

Power sources that enable in-body devices, such as implantable and ingestible devices, are provided. Aspects of the in-body power sources of the invention include a solid support, a first high surface area electrode and a second electrode. Embodiments of the in-power sources are configured to emit a detectable signal upon contact with a target physiological site. Also provided are methods of making and using the power sources of the invention.

DETAILED DESCRIPTION

Figure 1:
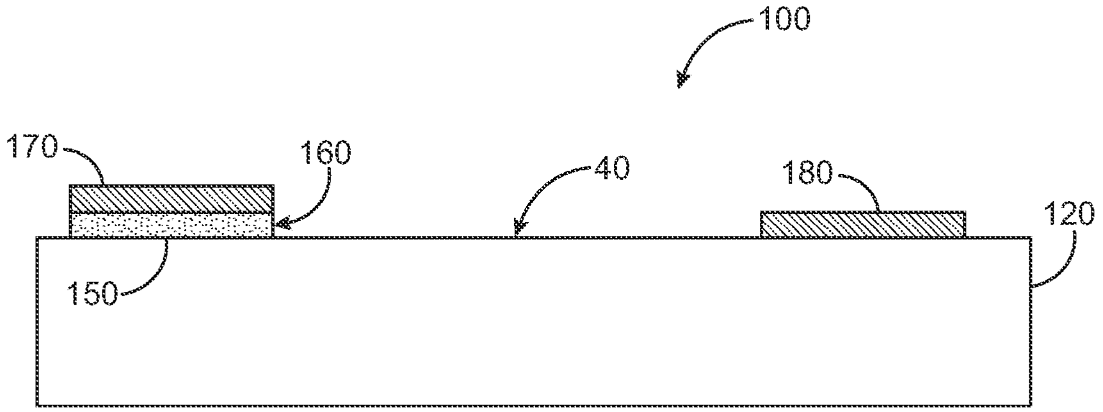
FIG. 1 shows one embodiment of a battery having a porous cathode under-layer according to one embodiment of the invention.

Power sources that enable in-body devices, such as implantable and ingestible devices, are provided. Aspects of the in-body power sources of the invention include a solid support, a first high surface area electrode and a second electrode. Embodiments of the in-power sources are configured to emit a detectable signal upon contact with a target physiological site. Also provided are methods of making and using the power sources of the invention.

In further describing the invention in greater detail, embodiments of the in-body power sources and in body devices that include the same are reviewed first, followed by a discussion of systems having devices that include the in-body power sources, and methods of using such devices and systems. Also reviewed in greater detail below are kits that include the devices having the in-body power sources of the invention.

In-Body Power Sources and Devices Including the Same

As summarized above, the invention provides power sources configured for use with in-body devices. An in-body device is a device that is configured to be used inside of a living body. Examples of in-body devices include, but are not limited to: implantable devices, e.g., implantable therapeutic devices, implantable diagnostic devices, e.g., sensors, etc; and ingestible devices, e.g., ingestible event markers (e.g., as described in greater detail below), etc.

In body power sources according to embodiments of the invention include a solid support; a first high surface electrode present on a surface of said solid support; and a second electrode. The solid support may vary depending on the nature of the device with which the in-body power source is to be employed. In certain embodiments, the solid support is small, e.g., where it is dimensioned to have a width ranging from about 0.01 mm to about 100 mm, e.g., from about 0.1 mm to about 20 mm, including from about 0.5 mm to about 2 mm; a length ranging from about 0.01 mm to about 100 mm, e.g., from about 0.1 mm to about 20 mm, including from about 0.5 mm to about 2 mm, and a height ranging from about 0.01 mm to about 10 mm, e.g., from about 0.05 mm to about 2 mm, including from about 0.1 mm to about 0.5 mm. The solid support element may take a variety of different configurations, such as but not limited to: a chip configuration, a cylinder configuration, a spherical configuration, a disc configuration, etc, where a particular configuration may be selected based on intended application, method of manufacture, etc. While the material from which the solid support is fabricated may vary considerably depending on the particular device for which the in-body power source is configured for use, in certain embodiments the solid support is made up of a semiconductor material, e.g., silicon. To provide for production of the porous under-layer, e.g., as described below, portions of the solid support surface may include a conductive material, e.g., metal or metal alloy, such as but not limited to gold, and the like.

In certain embodiments, the solid support is a semiconductor support that includes one or more circuit elements, where in certain embodiments the support is an integrated circuit. When present, integrated circuits include a number of distinct functional blocks, i.e., modules. Within a given solid support, at least some of, e.g., two or more, up to an including all of, the functional blocks, e.g., power source, processor, transmitter, etc., may be present in a single integrated circuit. By single integrated circuit is meant a single circuit structure that includes all of the different desired functional blocks for the device. In these embodiments, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention may be hybrid integrated circuits, which are miniaturized electronic circuits constructed of individual semiconductor devices, as well as passive components, bonded to a substrate or circuit board.

As mentioned above, one type of in-body device in which the power sources of the invention find use is an ingestible event marker. For ease of described, the in-body power sources will now be further described in terms of embodiments where the in body power source is part of an identifier of an ingestible event marker. However, as indicated above, the in-body power sources of the invention find use in devices other than ingestible event markers, and therefore in-body power sources of the invention are not limited to those configured for use in ingestible event markers (IEM).

The identifier of the IEM compositions is one that generates (i.e., emits) a detectable signal upon contact of the identifier with a target physiological site. The identifiers of the present compositions may vary depending on the particular embodiment and intended application of the composition so long as they are activated (i.e., turned on) upon contact with a target physiological location, e.g., stomach. As such, the identifier may be an identifier that emits a signal when it contacts a target body (i.e., physiological) site. The identifier may be any component or device that is capable of providing a detectable signal following activation, e.g., upon contact with the target site. In certain embodiments, the identifier emits a signal once the composition comes into contact with a physiological target site, e.g., the stomach. Depending on the embodiment, the target physiological site or location may vary, where representative target physiological sites of interest include, but are not limited to: a location in the gastrointestinal tract, such as the mouth, esophagus, stomach, small intestine, large intestine, etc. In certain embodiments, the identifier is configured to be activated upon contact with fluid in the target site, regardless of the particular composition of the target site.

Depending on the needs of a particular application, the signal obtained from the identifier may be a generic signal, e.g., a signal that merely identifies that the composition has contacted the target site, or a unique signal, e.g., a signal which in some way uniquely identifies that a particular ingestible event marker from a group or plurality of different markers in a batch has contacted a target physiological site. As such, the identifier may be one that, when employed with a batch of unit dosages, e.g., a batch of tablets, emits a signal which cannot be distinguished from the signal emitted by the identifier of any other unit dosage member of the batch. In yet other embodiments, the identifier emits a signal that uniquely identifies that particular identifier. Accordingly, in certain embodiments the identifier emits a unique signal that distinguishes one class of identifier from other types of identifiers. In certain embodiments, the identifier emits a unique signal that distinguishes that identifier from other identifiers. In certain embodiments, the identifier emits a signal that is unique, i.e., distinguishable, from a signal emitted by any other identifier ever produced, where such a signal may be viewed as a universally unique signal (e.g., analogous to a human fingerprint which is distinct from any other fingerprint of any other individual and therefore uniquely identifies an individual on a universal level). In one embodiment, the signal may either directly convey information about a given event, or provide an identifying code, which may be used to retrieve information about the event from a database, i.e., a database linking identifying codes with compositions.

The identifier may generate a variety of different types of signals, including but not limited to: RF signals, magnetic signals, conductive (near field) signals, acoustic signals, etc. Of interest in certain embodiments are the specific signals described in pending PCT application serial no. PCT/US2006/16370 filed on Apr. 28, 2006; the disclosures of various types of signals in this application being specifically incorporated herein by reference. The transmission time of the identifier may vary, where in certain embodiments the transmission time may range from about 0.1 μsec to about 48 hours or longer, e.g., from about 0.1 μsec to about 24 hours or longer, such as from about 0.1 μsec to about 4 hours or longer, such as from about 1 sec to about 4 hours, including about 1 minute to about 10 minutes. Depending on the given embodiment, the identifier may transmit a signal once or transmit a signal two or more times, such that the signal may be viewed as a redundant signal.

The identifiers of the present compositions may vary depending on the particular embodiment and intended application of the composition so long as they are activated (i.e., turned on) upon contact with a target physiological location, e.g., stomach. As such, the identifier may be an identifier that emits a signal when it contacts a target body (i.e., physiological) site. In addition or alternatively, the identifier may be an identifier that emits a signal when interrogated after it has been activated. Identifier components of embodiments of the invention have: (a) an activation component; and (b) a signal generation component, where the signal generation component is activated by the activation component to produce an identifying signal, e.g., as described above.

The activation component is a component that activates the signal generation element of the identifier to provide a signal, e.g., by emission or upon interrogation, following contact of the composition with a target physiological site of interest, such as the stomach. As reviewed in co-pending PCT application serial no. PCT/US2006/016370, activation of the identifier may be achieved in a number of different ways, where such approaches include, but are not limited to: battery completion, battery connection, etc. The different activation approaches disclosed in this co-pending application may be readily adapted to provide activation, as described herein, and as such are herein incorporated by reference in their entirety.

Embodiments of activation elements based on battery completion formats employ in body battery sources of the invention, where when activated the in-body batter power source includes, a cathode, an anode, and an electrolyte. In such embodiments, when the cathode and anode come into contact with stomach fluid, the stomach fluid acts as the electrolyte component of the battery, such that the added component of the stomach fluid thus completes the battery.

In certain embodiments, the battery that is employed is one that comprises two dissimilar electrochemical materials which constitute the two electrodes (e.g., anode and cathode) of the battery. When the electrode materials come in contact with the body fluid, such as stomach acid or other types of fluid (either alone or in combination with a dried conductive medium precursor), a potential difference, i.e., a voltage, is generated between the electrodes as a result of the respective oxidation and reduction reactions occurring at the two electrodes (such that a voltaic cell or battery is produced). Accordingly, in embodiments of the invention, in-body power sources are configured such that when the two dissimilar materials are exposed to the target site, e.g., the stomach, the digestive tract, etc., a voltage is generated. The two dissimilar materials in an electrolyte are at different potentials. In certain of these embodiments, the in-body battery power source may be viewed as a power source that exploits electrochemical reaction in an ionic solution such as gastric fluid, blood, or other bodily fluids and some tissues.

The dissimilar materials making up the electrodes can be made of any two materials appropriate to the environment in which the identifier will be operating. The active materials are any pair of materials with different electrochemical potentials. For instance, in some embodiments where the ionic solution comprises stomach acids, electrodes may be made of a noble metal (e.g., gold, silver, platinum, palladium or the like) so that they do not corrode prematurely. Alternatively, the electrodes can be fabricated of aluminum or any other conductive material whose survival time in the applicable ionic solution is long enough to allow the identifier to perform its intended function. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the battery electrodes. In certain embodiments, electrode materials are chosen to provide for a voltage upon contact with the target physiological site, e.g., the stomach, sufficient to drive the signal generation element of the identifier. In certain embodiments, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain embodiments, the voltage ranges from about 0.001 to about 10 volts, such as from about 0.01 to about 10 V.

Materials and pairings of interest include, but are not limited to those reported in Table 1 below.

TABLE 1

| | Anode | Cathode |
|---|---|---|
| Metals | Magnesium, Zinc Sodium (†), Lithium (†) Iron and alloys thereof, e.g., Al and Zn alloys of Mg | |
| Salts | | Copper salts: iodide, chloride, bromide, sulfate, formate, (other anions possible) $Fe^{3+}$ salts: e.g. orthophosphate, pyrophosphate, (other anions possible) Oxygen or hydrogen (††) on platinum, gold or other catalytic surfaces |
| Intercalation compounds | Graphite with Li, K, Ca, Na, Mg | Vanadium oxide Manganese oxide |

† Protected anodes: certain high energy anode material such as Li, Na, and other alkali metals are unstable in their pure form in the presence of water or oxygen. These may however be used in an aqueous environment if stabilized. One example of this stabilization is the so-called "protected lithium anode" developed by Polyplus Corporation (Berkeley, CA), where a polymer film is deposited on the surface of lithium metal to protect it from rapid oxidation and allow its use in aqueous environment or air ambient. (Polyplus has IP pending on this).

†† Dissolved oxygen can also serve as a cathode. In this case, the dissolved oxygen in the bodily fluids would be reduced to OH— at a suitable catalytic surface such at Pt or gold. Also of interest dissolved hydrogen in a hydrogen reduction reaction.

In certain embodiments, one or both of the metals may be doped with a non-metal, e.g., to enhance the voltage output of the battery. Non-metals that may be used as doping agents in certain embodiments include, but are not limited to: sulfur, iodine and the like.

In certain embodiments, the electrode materials are cuprous iodine (CuI) or cuprous chloride (CuCl) as the cathode and magnesium (Mg) metal or magnesium alloy as the anode. Embodiments of the present invention use electrode materials that are not harmful to the human body.

As summarized above, in-body power sources of the invention, such as batteries that include electrodes of two dissimilar materials (as reviewed immediately above) include at least one a high surface area electrode, e.g., a high surface area cathode and/or high surface area anode. By high surface area electrode is meant an electrode having a surface area that is about 2-fold or greater, such at about 10-fold or greater, than the area of the surface of a solid support that is covered by the electrode in the power source, e.g., battery. In certain embodiments, the surface area of the electrode ranges from about 0.01 $mm^2$ to about 100 $mm^2$, such as from about 0.1 $mm^2$ to about 50 $mm^2$ and including from about 1 $mm^2$ to about 10 $mm^2$. In certain embodiments, the high surface area electrode is obtained by having an electrode that is made up of an active electrode material (e.g., where illustrative active cathode and anode materials are provided above) present on a porous under-layer. In certain embodiments, all of the electrodes are high surface area electrodes, while in other embodiments only some of the electrodes, e.g., one of the electrodes, are high surface area electrodes.

Depending on the particular embodiment, the cathode and anode may be present on the same support or different supports, e.g., where two or more different supports are bonded together to produce the battery structure, e.g., as is present in a "flip-chip" embodiment. Similarly, the number of cathodes and anodes in a given battery may vary greatly depending on the embodiment, e.g., where a given embodiment may include a single battery having one anode and cathode, a single battery having multiple anodes and/or cathodes, or two or more distinct batteries each made up of one or more cathodes and/or anodes. Battery configurations of interest include, but are not limited to, those disclosed in PCT application serial no. PCT/US2006/016370 filed on Apr. 28, 2006 and entitled PHARMA-INFORMATICS SYSTEM; PCT application serial no. PCT/US2007/022257 filed on Oct. 17, 2007 and entitled IN-VIVO LOW VOLTAGE OSCILLATOR FOR MEDICAL DEVICES; PCT application serial no. PCT/US2007/82563 filed on Oct. 25, 2007 and entitled CONTROLLED ACTIVATION INGESTIBLE IDENTIFIER; U.S. patent application Ser. No. 11/776,480 filed Jul. 11, 2007 entitled ACOUSTIC PHARMA INFORMATICS SYSTEM; and PCT application serial no. PCT/US2008/52845 filed on Feb. 1, 2008 and entitled INGESTIBLE EVENT MARKER SYSTEMS; the disclosures of which applications (and particularly battery configurations disclosed therein) are herein incorporated by reference.

FIG. 1 provides a schematic illustration of battery power source according to an embodiment of the invention that includes a high surface area electrode, and specifically a high surface area cathode. The battery 100 shown in FIG. 1 includes a solid support 120 having an upper surface 140. Present on the upper surface 140 is cathode 160 and anode 180. Cathode 160 includes porous under-layer 150 and active cathode material 170. Each of these elements is now described in greater detail below. While the embodiment depicted is where the cathode includes a porous under-layer, in certain embodiments it is the anode that includes a porous underlay, while in yet other embodiments both a cathode and anode have the porous under-layer. Both the cathode and anode are present on a surface of a solid support. In certain embodiments such as that shown in FIG. 1, the two electrodes are present on the same surface of the solid support. In yet other embodiments, the two electrodes may be present on different surfaces of the support, e.g., opposite surfaces of the support.

The porous under-layer 150 is a layer that mechanically supports the active electrode (e.g., cathode) material 170, improves adhesion and/or increases the surface area of the electrode, and provides for current passage between the cathode material and elements, e.g., circuitry, present on the solid support 120 (described in greater detail below). The porous under-layer may be fabricated from a variety of different materials, such as conductive materials, e.g., copper, titanium, aluminum, graphite, gold, platinum, iridium, etc., where the materials may be pure materials or materials made up of two or more elements, e.g., as found in alloys, etc. With respect to a cathode, materials of interest for a cathode porous under-layer include, but are not limited to: Au, Cu, Pt, Ir, Pd, Rh, Ru, as well as binary and ternary alloys thereof. With respect to the anode, materials of interest for an anode porous under-layer include, but are not limited to: Ti and alloys thereof (e.g., Ti—W, Ti—Cr, TiN), W, W—C, etc. The thickness of the under-layer may vary, where in certain embodiments the thickness ranges from about 0.01 to about 100 μm, such as from about 0.05 to about 50 μm and including from about 0.01 to about 10 μm. The dimensions of the porous under-layer with respect to length and width on the surface of the solid support may or may not be coextensive with the same dimensions of the active cathode material, as desired.

As summarized above, the under-layer may be rough or porous. The porosity or roughness of the under-layer may vary, so long as it imparts the desired surface area to the electrode, e.g., cathode. In certain embodiments, the porosity or roughness of the under-layer is chosen to provide an effective surface area enhancement of about 1.5 times or more to about 1000 times or more, e.g., from about 2 to about 100 time or more, such as from about 2 to about 10 times or more, greater than that obtained from a comparable electrode that lacks the porous under-layer. Surface area enhancement can be determined by comparing the electrochemical capacitance or cyclic voltammogram of the rough or porous electrode with that of a smooth electrode of the same material. Roughness may also be determined by other techniques, such as atomic force microscopy (AFM), electron microscopy, electrochemical impedance spectroscopy or Brunauer-Emmett-Teller (BET) analysis.

The porous cathode under-layer may be produced using any convenient protocol. In certain embodiments, planar processing protocols are employed. Planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electrodeposition (e.g., electroplating), cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), electrodissolution/electropolishing (a metal is deposited, then selective areas are dissolved to make it rough and porous), etc. Another protocol of interest is electroless plating as a deposition method. In these deposition protocols, metal is deposited out of solution by a reducing agent. The deposited metal layer can be used to coat an already existing rough nonconductive/poorly conductive surface layer or particles such as carbon, alumina, polymers, zeolite, silicon oxide, amorphous carbon and nanotubes. The nonconductive layer can be deposited via any suitable planar processing method, such as cathodic arc, electrophoretic deposition, or a paste/glue containing particles. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in copending PCT application serial no. PCT/US2006/016370; the disclosure of which is herein incorporated by reference.

For the porous under-layer, in certain embodiments an electrodeposition protocol is employed. Where the porous cathode under-layer comprises a metal(s), electroplating (electrodeposition of metals) may be employed. In certain embodiments, the electroplating protocol employed is one in which the current density and/or agitation of the solution is selected so as to impart the desired roughness or porosity to the deposited porous cathode under-layer. In certain embodiments, the metal, e.g., copper, film is deposited in an electroplating bath at the mass-transfer limit. The phrase "mass transfer limit" means that the current density is optimized along with the metal ion concentration in the bath and the flow rate of the bath, such that depositing occurs at substantially the maximum limit at which metal ions can arrive at the surface. Deposition at the mass transfer limit yields, in certain embodiments, a dendritic form of deposited material. Depending on the particular metal and ion concentration thereof, the current density may vary. In certain of the embodiments, the selected current density ranges from about 5 to about 2000 $mAmps/cm^2$, such as from about 50 to about 400 $mAmps/cm^2$, e.g., about 200 $mAmps/cm^2$. Plate up may be carried out in a suitable plating cell, such as a plating tank with agitation, a paddle cell, or a fountain cell. The fluid flow may be selected in conjunction with the applied current density to achieve the desired porosity or roughness. In a plating tank with a rotary mixer, the stirring rate may be between about 0 and about 200 rpm, such as between about 50 to about 500 rpm. With respect to the metal ion concentration, a relatively lower metal ion concentration may be employed to obtain a rough deposit at a lower current density while relatively higher ion concentration may be employed to obtain a rough deposit at a higher current density. In certain embodiments, the metal ion concentration ranges from 0.001 mol/L to 4 mol/L, such as from 0.05 mol/L to 1 mol/L. Flow rate employed during deposition also impacts the nature of the film that is deposited. Lower flow rates can be used lower current densities.

Where desired, various additives may be included in the electroplating fluid to enhance the desired porosity. Additives that may be included in the solution include, but are not limited to: organic acids, e.g., acetic acid, citric acid, e.g., polymers, e.g., PEG, etc. The plating up solution may also contain alcohols, e.g., ethanol), amines and thiols (e.g., thiourea). Typical copper plating bath compositions (such as acidic, e.g., sulfuric acid/copper sulfate) and alkaline (e.g., pyrophosphate or chromate solutions) may also be used. Where polymers are added, the polymers may be linear or branched water-soluble polymers, such as a poly(alkylene glycol), such as poly(ethylene glycol) (PEG). Other related polymers are also suitable for use in the practice of this invention and that the use of the term PEG or poly(ethylene glycol) is intended to be inclusive and not exclusive in this respect. In some embodiments, the polymer has from 2 to about 300 termini. In some embodiments, the polymer is clear, colorless, odorless, soluble in water, stable to heat, inert to many chemical agents, does not hydrolyze or deteriorate, and is nontoxic. In some embodiments, the polymer is biocompatible, which is to say that the polymer is capable of coexistence with living tissues or organisms without causing harm. In some embodiments, the polymer is non-immunogenic, which is to say that the polymer does not produce an immune response in the body. In some embodiments, the polymer is a PEG comprising the formula Ra—$(CH_2CH_2O)$m-$CH_2CH_2$—, where m is from about 3 to about 4000, or from about 3 to about 2000, and Ra is a hydrogen, —OH, $CH_3$—O—, $CH_2CH_2$—O— or $CH_3CH_2CH_2$—O—. The polymer can be linear or branched. In some embodiments, a branched polymer has a central branch core moiety and a plurality of linear polymer chains linked to the central branch core. PEG includes branched forms that can be prepared by addition of ethylene oxide to various polyols, such as glycerol, pentaerythritol and sorbitol. The branched PEGs can be represented in general form as Rb(-PEG-OH)n in which Rb represents the core moiety, such as glycerol or pentaerythritol, and n represents the number of arms and is from 2 to 300. In some embodiments, the PM is a linear or branched PEG. Suitable polymers that can be employed include, but are not limited to, poly (alkylene glycol), such as poly(ethylene glycol) (PEG) and poly(propylene glycol) (PPG), copolymers of ethylene glycol and propylene glycol and the like, poly(oxyethylated polyol), poly(olefinic alcohol), poly(vinylpyrrolidone), poly (hydroxypropylmethacrylamide), poly(α-hydroxy acid), poly(vinyl alcohol), polyphosphazene, polyoxazoline, and copolymers, terpolymers, derivatives and mixtures thereof. The molecular weight of each chain of the polymer can vary in the range of from about 100 Da to about 100,000 Da, or from about 6,000 Da to about 80,000 Da. Suitable PEGs include, but are not limited to, PEG(100), PEG(200), PEG (300), PEG(400), PEG(600), PEG(1000), PEG(1500), PEG (2000), PEG(3000), PEG(3350), PEG(4000), PEG(5000), PEG(6000), PEG(8000), and PEG(10000), and methoxy and ethoxy derivatives thereof, and any PEG having a molecular size within and inclusive of any of the above indicated molecular weights. The polymer component may be synthesized using any convenient protocol or purchased from a commercial source, as desired. Suitable PEGs are commercially available from many sources, such as Sigma-Aldrich Corp. (St. Louis, Mo.).

Additives of interest include, but are not limited to, accelerator, suppressors, wetting agents, levelers and bath stabilizers. Accelerators of interest include, but are not limited to: thiols, such as thiourea and 3-sulfopropyldisulfide, where accelerators of interest, either by themselves or in combination with other additives, accelerate metal, e.g., copper, deposition rate. In certain embodiments, the accelerator additive is present at a concentration ranging from 1 ppB to 1000 ppm, such as 10 ppb to 500 ppm. In certain embodiments, the concentration of additive is employed in combination with a flow rate the provides for dendritic nodules that grow at a substantially exponential rate, e.g., where the end of the dendrite is present in a relatively rich accelerator environment and the opposite end of the dendrite proximal to the surface is present in a relatively poor accelerator environment. In certain of these embodiments, the flow rate is set to have a certain diffusion layer thickness which provides for this type of growth, where the diffusion layer thickness may range from 0.01 to 500 μm, such as 1 to 100 μm.

In certain embodiments, accelerating additives are employed in combination with suppressing additives. Suppressing additives of interest are compounds that physically block the surface of the metal, where such additives include, but are not limited to: polyethelene glycol, amino compounds and organic compounds. By physically blocking the surface of the solid support, growth at the surface distal ends of the deposited structures may be enhanced relative to growth at the surface proximal ends.

In these embodiments, concentrations and types of accelerating additives may be employed that eliminate the impact of suppressing additives, where the accelerators dislodge the suppressors. In certain of these embodiments, a solution is employed that has a suppressing additive and an accelerating additive, where the concentration of the suppressing additive is mass-transfer limited. Any part of the solution that gets a little bit of a nodule going will reach into a higher concentration region of accelerant and then will grow exponentially to provide a desired amount of roughness. In these embodiments, the area close to the surface is heavily suppressed by the suppressor agent. The parts of the growing nodules that stick up into the solution come into contact with an accelerating agent that can come in and dislodge the suppressing agent, and provide the desired dendritic format or nodules.

An alternative to employing a suppressing agent, e.g., as described above, is to employ a protocol that includes co-evolution of gas, where blocking gas bubbles are produced at the surface of the solid support during deposition. In these embodiments, the deposition conditions are chosen that generate a gas, e.g., hydrogen gas, at he surface of the solid support upon which the metal is being deposited. Where desired, the size of the bubbles that are produced in these protocols may be modulated by employing a surface tension agent, e.g., acetic acid, polyethylene glycol, or other agents that control the wetting properties in a manner that provides for bubbles of desired dimension. Relatively less wetting agent can be employed to provide for larger, e.g., micron, sized pores, while relatively more wetting agent can be employed for smaller sized pores.

The gas coevolution protocol may be employed with appropriate accelerator agents in a manner analogous that described above with respect to suppressor agents, as both approaches physically block the surface of the solid support and the presence of the accelerator may be employed to enhance growth at the surface distal ends of the deposited structures. Accordingly, when current to the entire surface of the solid support, the metal, e.g., copper will preferentially plate where there is accelerating species as opposed to in the regions, e.g., valleys between deposited structure, where there is no accelerating species, e.g., because of presence of physical blocking agent, such as a bubble or suppressor species.

In yet another embodiment, a self-assembled monolayer, or an electro-grafted layer, which is an organic, diazonium containing species that can actually covalently bond to the surface of the solid support may be employed. In manner similar to the bubbles and suppressors described above, such deposited species can also physically block the surface to modulate the form of the plated structures and provide the desired porous structure. By controlling the concentration of the nuclei of the electrographic layer, or the density of the self-assembled mono layer, one can modulate the nature of the deposited metal structures. In certain embodiments, these protocols are employed where a metal different from that of the solid support is being deposited on the solid support. In certain embodiments, a masking approach is employed to further modulate the nature of the deposited structures on the surface of the solid support.

In yet other embodiments, a cathodic arc deposition protocol is employed to produce the desired porous cathode under-layer. In such protocols, a cathodic arc generated metallic ion plasma is contacted with a surface of a substrate under conditions sufficient to produce the desired structure of the porous cathode under-layer, e.g., as described above. The cathodic arc generated ion plasma beam of metallic ions may be generated using any convenient protocol. In generating an ion beam by cathodic arc protocols, an electrical arc of sufficient power is produced between a cathode and one or more anodes so that an ion beam of cathode material ions is produced. Prior to deposition of the cathodic arc metal, a seed metal layer is produced from at least one, but often two or more, conformal metal under-layers. These under-layers start with a thin adhesion layer that contains metals including but not limited to TiN, Ti, W, Cr or alloys of these metals. This first metal layer improves adhesion of the thicker cathodic arc metal and may be sealed with a noble metal that includes, but is not limited to, Au, Pt, Ag, Cu, Pt, Ir, Pd, Rh, or Ru or alloys of these metals. The cap metal seals the adhesion metal chemically and is chosen to also adhere well to the thicker metal deposited by the cathodic arc process. The cathodic arc can be run in a variety of conditions, including but not limited to higher pressure of inert gas (gas could be Ar, Ne, He, Xe or a simple mixture of these; pressures can range over 50 mT up to 1000 mT) and a neutral (unbiased) target. In the case of a higher pressure and a neutral target, this suppresses small ionized metal particles in favor of larger macro particles at the target surface during film growth, resulting in a film that can have peak-to-peak roughness values ranging from 0.2 to 10 times the average deposited film thickness. Films grown can be as thin as 0.25 um and up to 25 um, and in certain embodiments are in the range of 3 to 10 um thick before they achieve a desired roughness for the underlying electrode structure. Other convenient protocols for producing a structure via cathodic arc deposition may be employed, where protocols known in the art which may be adapted for use in the present invention include, but are not limited to those described in U.S. Pat. Nos. 6,929,727; 6,821,399; 6,770,178; 6,702,931; 6,663,755; 6,645,354; 6,608,432; 6,602,390; 6,548,817; 6,465,793; 6,465,780; 6,436,254; 6,409,898; 6,331,332; 6,319,369; 6,261,421; 6,224,726; 6,036,828; 6,031,239; 6,027,619; 6,026,763; 6,009,829; 5,972,185; 5,932,078; 5,902,462; 5,895,559; 5,518,597; 5,468,363; 5,401,543; 5,317,235; 5,282,944; 5,279,723; 5,269,896; 5,126,030; 4,936,960; and Published U.S. Application Nos.: 2005/0249983; 2005/0189218; 2005/0181238; 2004/0168637; 2004/0103845; 2004/0055538; 2004/0026242; 2003/0209424; 2002/0144893; 2002/0140334 and 2002/0139662; the disclosures of which are herein incorporated by reference. Such protocols are of interest in the deposition of a variety of different materials, e.g., copper, titanium, aluminum, etc. Additional cathodic arc protocols and structures produced thereby include, but are not limited to, those described in published PCT application No. WO 2007/149546 titled IMPLANTABLE MEDICAL DEVICES COMPRISING CATHODIC ARC PRODUCED STRUCTURES, the disclosure of which is herein incorporated by reference.

In yet other embodiments an electrophoretic deposition protocol may be employed. Electrophoretic deposition (EPD) is a term for a broad range of industrial processes which includes electrocoating, electrophoretic coating, or electrophoretic painting. In EPD, colloidal particles suspended in a liquid medium migrate under the influence of an electric field (electrophoresis) and are deposited onto a conductive surface. All colloidal particles that can be used to form stable suspensions and that can carry a charge can be used in electrophoretic deposition. This includes material classes such as polymers, pigments, dyes, ceramics and metals. For example, where the material to be deposited is graphite, a suspension of graphite particles may be produced, where surfactants may be included in the suspension to impart a desired charge to the graphite particles. Sizes for the graphite particles may vary, and in certain embodiments may range from about 0.1 to about 100 μm, such as from about 0.1 to about 2 μm. Any convenient surfactant may be includes that is capable of imparting the desired charge to the graphite particles in suspension, including ionic and non-ionic surfactants. An electric field may then be applied to the suspension, where the applied electric field is sufficient to cause the graphite particles to migrate to the surface of the support and be deposited in the form of the desired porous under-layer.

In yet other embodiments, the solid support surface is electrochemically modified, e.g., via electrochemical dissolution, where portions of the surface are selectively removed to provide for the desired porous structure. For example, an anodic potential may be applied to a metal surface to dissolve the metal surface. Such an approach may be employed in combination with a patterning photo-resist layer and/or with additives to generate a desired roughness or pattern of nodules on the surface. In certain of these embodiments, a metal layer is first deposited, e.g., by any convenient deposition protocol. Next, additives and/or masking (e.g., photoresist) is employed to selectively dissolve certain areas of the surface and make the surface rough.

In certain embodiments, a metal codeposition and dissolution approach is employed. In these embodiments, two metals are simultaneously deposited, e.g., via cathodic arc, evaporation, sputtering, etc.) to make a composite layer, where the metals are (1) an inert electrode metal, such as Pt, PtIr, Ir, Au, or Cu and (2) a highly oxidizable and soluble metal, such as Mg, Zn, Li. The resulting deposited layer is a composite, consisting of mostly metal 1, but with isolated domains of metal 2. The layer is then immersed in an electrolytic solution (e.g., a solvent such as water or an organic acid (such as sulfuric, nitric or hydrochloric acids), bases (such as NaOH, aluminum etchant), neutral salts (such as NaCl, KCl, $CuSO_4$, magnesium, lithium, zinc salts), or organic additives and surfactants (such as polyethylene glycol). Upon immersion, metal 2 dissolves away leaving behind a film of metal 1 that includes pores. The size of the pores will be that of the particles of metal (2). In certain embodiments, e.g., where one does not wish to leave any of metal 2 behind inside the film, the second metal's deposition conditions (deposition current, filtering, cathode temperature, etc) are set to yield particles that are on the order of the total desired film thickness. The first metal particles may be selected to be smaller and more compact than those of the second metal. Cathodic arc is particularly suitable for the composite film deposition because it allows deposition of particles with controlled particle size. The dissolution step may be carried out with an applied current (anodic dissolution), or it can be done without an applied current in which case it is a result of the chemical reaction between metal 2 and solution components and/or a galvanic couple between metal 1 and metal 2 that forces metal 2 to corrode. The above approach can also be applied to non-metallic rough films, e.g., any pair of materials deposited via cathodic arc where one of them can be selectively dissolved or etched away leaving behind a porous layer. Also, the above approach is not limited to two metals, i.e. 2 or more metals (or alloys) can be included in the composite film.

Present on top of the porous under-layer is the active electrode (e.g., cathode) material. As reviewed above, the active electrode material may comprise a variety of different materials. Where the electrode is a cathode, in certain embodiments, the cathode material includes copper, where of particular interest in certain embodiments are cuprous iodide (CuI) or cuprous chloride (CuCl) as the cathode material. Where desired, e.g., to enhance voltage of the battery, the active material may be doped with additional elements, e.g., sulfur, etc.

The active cathode material may be provided onto the porous under-layer using any convenient protocol. In certain embodiments, a deposition protocol is employed, such as electrodeposition, e.g., electroplating, or evaporation, e.g., chemical vapor deposition.

Also present in the battery is at least one anode. As reviewed above, the anode material may comprise a variety of different materials. In certain embodiments, the anode material includes magnesium (Mg) metal or magnesium alloy. The active anode material may be provided onto the porous under-layer using any convenient protocol. In certain embodiments, a deposition protocol is employed, such as electrodeposition, e.g., electroplating, or evaporation, e.g., chemical vapor deposition.

As reviewed above, in certain embodiments, the solid support 120 is a circuitry support element. The circuitry support element may take any convenient configuration, and in certain embodiments is an integrated circuit (IC) chip. The surface upon which the electrode elements are positioned may be the top surface, bottom surface or some other surface, e.g., side surface, as desired, where in certain embodiments the surface upon which the electrode elements are at least partially present is a top surface of an IC chip.

In addition to the battery component of the identifier, described above, identifiers of the invention also include a signal generation component. The signal generation component of the identifier element is a structure that, upon activation by the activation component, emits a detectable signal, e.g., that can be received by a receiver, e.g., as described in greater detail below. The signal generation component of certain embodiments can be any convenient device that is capable of producing a detectable signal and/or modulating transduced broadcast power, upon activation by the activation component. Detectable signals of interest include, but are not limited to: conductive signals, acoustic signals, etc. As reviewed above, the signals emitted by the signal generator may be generic or unique signals, where representative types of signals of interest include, but are not limited to: frequency shift coded signals; amplitude modulation signals; frequency modulation signals; etc.

In certain embodiments, the signal generation element includes circuitry, as developed in more detail below, which produces or generates the signal. The type of circuitry chosen may depend, at least in part, on the driving power that is supplied by the power source of the identifier. For example, where the driving power is 1.2 volts or above, standard CMOS circuitry may be employed. In other embodiments where the driving power ranges from about 0.7 to about 1.2 V, sub-threshold circuit designs may be employed. For driving powers of about 0.7 V or less, zero-threshold transistor designs may be employed.

In certain embodiments, the signal generation component includes a voltage-controlled oscillator (VCO) that can generate a digital clock signal in response to activation by the activation component. The VCO can be controlled by a digital circuit, which is assigned an address and which can control the VCO with a control voltage. This digital control circuit can be embedded onto a chip that includes the activation component and oscillator. Using amplitude modulation or phase shift keying to encode the address, an identifying signal is transmitted.

The signal generation component may include a distinct transmitter component that serves to transmit the generated signal to a remote receiver, which may be internal or external to the patient, as reviewed in greater detail below. The transmitter component, when present, may take a number of different configurations, e.g., depending on the type of signal that is generated and is to be emitted. In certain embodiments, the transmitter component is made up of one or more electrodes. In certain embodiments, the transmitter component is made up of one or more wires, e.g., in the form of antenna(e). In certain embodiments, the transmitter component is made up of one or more coils. As such, the signal transmitter may include a variety of different transmitters, e.g., electrodes, antennas (e.g., in the form of wires) coils, etc. In certain embodiments, the signal is transmitted either by one or two electrodes or by one or two wires. A two-electrode transmitter is a dipole; a one electrode transmitter forms a monopole. In certain embodiments, the transmitter only requires one diode drop of power. In some embodiments, the transmitter unit uses an electric dipole or electric monopole antenna to transmit signals.

Figure 2:
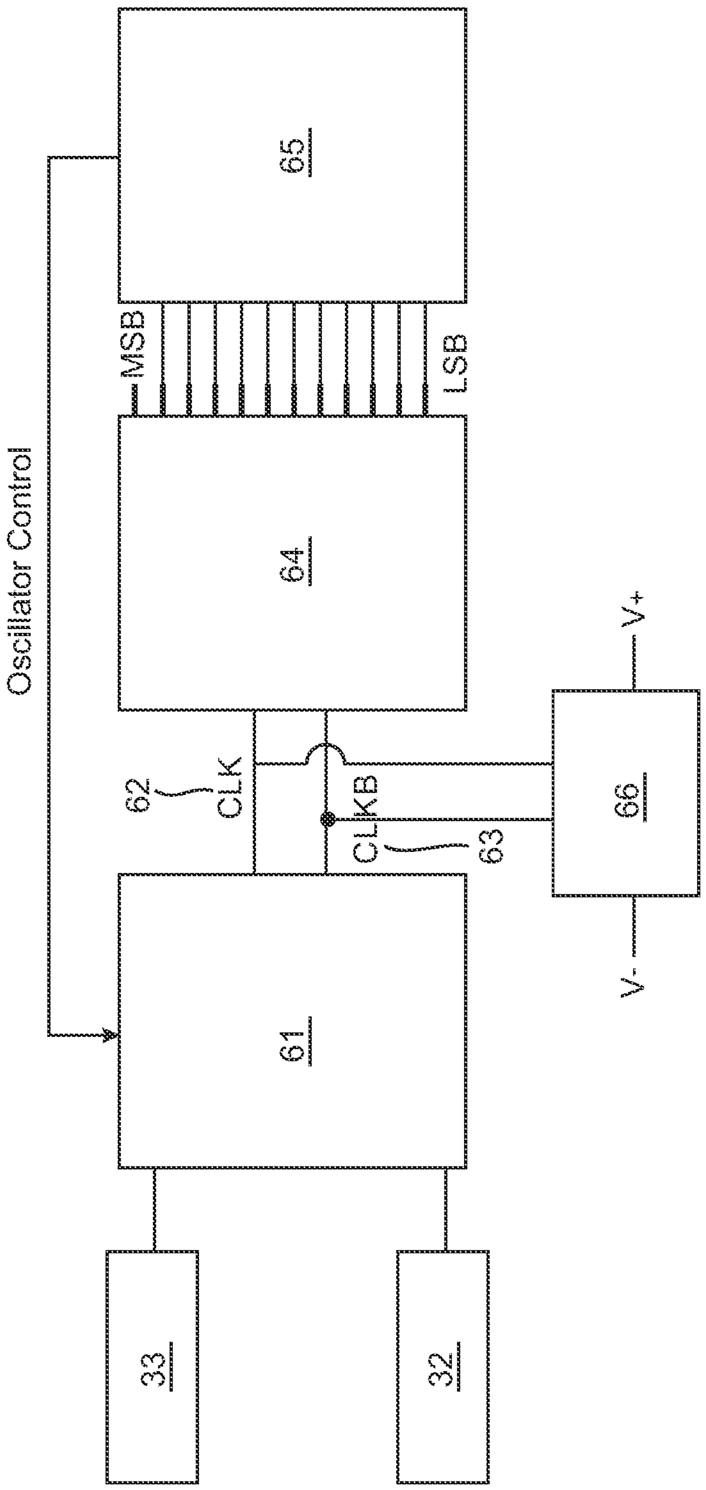
FIG. 2 provides detail of certain implementations of an electronic circuit of various embodiments of the invention.

FIG. 2 shows the detail of one implementation of an electronic circuit that can be employed in an identifier according to the present invention. On the left side are the two battery electrodes, metal 1 and metal 2 (32 and 33). These metals, when in contract with an electrolyte (produced upon contact with target site fluid, either alone or in combination with dried conductive medium precursor, as reviewed above), form a battery that provides power to an oscillator 61, in this case shown as a schematic. The metal 1 32 provides a low voltage, (ground) to the oscillator 61. Metal 2 33 provides a high voltage ($V_{high}$) to the oscillator 61. As the oscillator 61 becomes operative, it generates a clock signal 62 and an inverted clock signal 63, which are opposites of each other. These two clock signals go into the counter 64 which simply counts the number of clock cycles and stores the count in a number of registers. In the example shown here, an 8 bit counter is employed. Thus, the output of counter 64 begins with a value of "00000000," changes to "00000001" at the first clock cycle, and continues up to "11111111." The 8-bit output of counter 64 is coupled to the input of an address multiplexer (mux) 65. In one embodiment, mux 65 contains an address interpreter, which can be hard-wired in the circuit, and generates a control voltage to control the oscillator 61. Mux 65 uses the output of counter 64 to reproduce the address in a serial bit stream, which is further fed to the signal-transmission driving circuit. Mux 65 can also be used to control the duty-cycle of the signal transmission. In one embodiment, mux 65 turns on signal transmission only one sixteenth of the time, using the clock counts generated by counter 64. Such a low duty cycle conserves power and also allows other devices to transmit without jamming their signals. The address of a given chip can be 8 bits, 16 bits or 32 bits. Where desired, more than 8 bits may be used in a product, e.g., where the identifiers are employed with different types of pharmaceutical agents and each pharmaceutical is desired to have its own specific address.

According to one embodiment, mux 65 produces a control voltage, which encodes the address serially and is used to vary the output frequency of oscillator 61. By example, when the control voltage is low, that is, when the serial address bit is at a 0, a 1 megahertz signal is generated by the oscillator. When the control voltage is high, that is, when the address bit is a 1, a 2 megahertz signal is generated the oscillator. Alternately, this can be 10 megahertz and 20 megahertz, or a phase shift keying approach where the device is limited to modulating the phase. The purpose of mux 65 is to control the frequency of the oscillator or an AC alternative embodiment of the amplified signal of oscillation.

The outputs of mux 65 are coupled to electrode drive 66 which can drive the electrodes to impose a differential potential to the solution, drive an oscillating current through a coil to generate a magnetic signal, or drive a single electrode to push or pull charge to or from the solution. In this manner, the device broadcasts the sequence of 0's and 1's which constitute the address stored in mux 65. That address would be broadcast repeatedly, and would continue broadcasting until metal 1 or metal 2 (32 and 33) is consumed and dissolved in the solution, when the battery no longer operates.

Other configurations for the signal generation component are of course possible. Other configurations of interest include, but are not limited to, those described in PCT application serial no. PCT/US2006/016370 filed on Apr. 28, 2006 and entitled PHARMA-INFORMATICS SYSTEM; PCT application serial no. PCT/US2007/022257 filed on Oct. 17, 2007 and entitled IN-VIVO LOW VOLTAGE OSCILLATOR FOR MEDICAL DEVICES; PCT application serial no. PCT/US2007/082563 filed on Oct. 25, 2007 and entitled CONTROLLED ACTIVATION INGESTIBLE IDENTIFIER; U.S. patent application Ser. No. 11/776,480 filed Jul. 11, 2007 entitled ACOUSTIC PHARMA INFORMATICS SYSTEM; and PCT application serial no. PCT/US2008/052845 filed on Feb. 1, 2008 and entitled INGESTIBLE EVENT MARKER SYSTEMS; the disclosures of which applications (and particularly signal generation components thereof) are herein incorporated by reference.

The identifiers may be fabricated using any convenient processing technology. In certain embodiments, planar processing protocols are employed to fabricate power sources having surface electrodes, where the surface electrodes include at least an anode and cathode at least partially on the same surface of a circuitry support element. In certain embodiments, planar processing protocols are employed in a wafer bonding protocol to produce a battery source. Planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electrodeposition (e.g., electroplating), cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in copending PCT application serial no. PCT/US2006/016370; the disclosure of which is herein incorporated by reference.

Optional Physiologically Acceptable Carrier Component

Identifiers of the invention that include in-body power sources as described above may be present in (i.e., combined with) a physiologically acceptable carrier component, e.g., a composition or vehicle that aids in ingestion of the identifier and/or protects the identifier until it reaches the target site of interest. By physiologically acceptable carrier component" is meant a composition, which may be a solid or fluid (e.g., liquid), which has is ingestible.

Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

A liquid composition may comprise a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener.

A composition in the form of a tablet or pill can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the polyorthoester. The rate of hydrolysis in turn may be controlled by the composition of the polyorthoester and the number of hydrolysable bonds in the polyorthoester. Other factors determining the rate of release of an active agent from the present pharmaceutical composition include particle size, acidity of the medium (either internal or external to the matrix) and physical and chemical properties of the active agent in the matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are *acacia*, methylcellulose, sodium carboxymethylcellulose, poly-vinylpyrrolidone (Povidone), hydroxypropyl methyl-cellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

Other components suitable for use in the formulations of the present invention can be found in Remington's Pharmaceutical Sciences, Mace Publishing Company, Philadelphia, Pa., 17th ed. (1985).

Optional Active Agent

In certain embodiments, the identifier is not associated with a pharmaceutically active agent. As such, the identifier, and any carrier or other component that make up the ingestible event marker, do not include an active agent.

In yet other embodiments, the identifier is associated with an active agent, e.g., where the active agent is present in the carrier composition that includes the identifier. By "active agent/carrier component" is meant a composition, which may be a solid or fluid (e.g., liquid), which has an amount of active agent, e.g., a dosage, present in a pharmaceutically acceptable carrier. The active agent/carrier component may be referred to as a "dosage formulation."

"Active agent" includes any compound or mixture of compounds which produces a physiological result, e.g., a beneficial or useful result, upon contact with a living organism, e.g., a mammal, such as a human. Active agents are distinguishable from such components as vehicles, carriers, diluents, lubricants, binders and other formulating aids, and encapsulating or otherwise protective components. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication. In certain embodiments, the active agent may be a chemical substance, such as a narcotic or hallucinogen, which affects the central nervous system and causes changes in behavior.

The active agent (i.e., drug) is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

The active agent (i.e., drug) may include one or more functional groups necessary for structural interaction with the target, e.g., groups necessary for hydrophobic, hydrophilic, electrostatic or even covalent interactions, depending on the particular drug and its intended target. Where the target is a protein, the drug moiety may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Drugs of interest may include cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The active agent may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the active agent may be obtained from a library of naturally occurring or synthetic molecules, including a library of compounds produced through combinatorial means, i.e., a compound diversity combinatorial library. When obtained from such libraries, the drug moiety employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc.

A variety of manufacturing protocols may be employed to produce compositions as described above, e.g., where an identifier is present in pharmaceutically acceptable carrier or vehicle, where the carrier or vehicle may further include one or more active agents. In manufacturing such compositions, an identifier is stably associated with the pharmaceutical dosage from in some manner. By stably associated is meant that the identifier and the dosage form do not separate from each other, at least until administered to the subject in need thereof, e.g., by ingestion. The identifier may be stably associated with the pharmaceutical carrier/active agent component of the composition in a number of different ways. In certain embodiments, where the carrier/active agent component is a solid structure, e.g., such as a tablet or pill, the carrier/active agent component is produced in a manner that provides a cavity for the identifier. The identifier is then placed into the cavity and the cavity sealed, e.g., with a biocompatible material, to produce the final composition. For example, in certain embodiments a tablet is produced with a die that includes a feature which produces a cavity in the resultant compressed tablet. The identifier is placed into the cavity and the cavity sealed to produce the final tablet. In a variation of this embodiment, the tablet is compressed with a removable element, e.g., in the shape of a rod or other convenient shape. The removable element is then removed to produce a cavity in the tablet. The identifier is placed into the cavity and the cavity sealed to produce the final tablet. In another variation of this embodiment, a tablet without any cavity is first produced and then a cavity is produced in the tablet, e.g., by laser drilling. The identifier is placed into the cavity and the cavity sealed to produce the final tablet. In yet other embodiments, a tablet is produced by combining the identifier with subparts of the tablet, where the subparts may be pre-made subparts or manufactured sequentially. For example, in certain embodiments tablets are produced by first making a bottom half of the tablet, placing the signal generation element on a location of the bottom half of the tablet, and then placing top portion of the tablet over the bottom half and signal generation element to produce the final desired composition. In certain embodiments, a tablet is produced around an identifier such that the identifier is located inside of the produced tablet. For example, an identifier, which may or may not be encapsulated in a biocompatible compliant material, e.g., gelatin (to protect the signal generation element), is combined with carrier/active agent precursor, e.g., powder, and compressed or molded into a tablet in a manner such that the identifier is located at an internal position of the tablet. Instead of molding or compressing, the carrier/active agent component is, in certain embodiments, sprayed onto an identifier in a manner that builds up the tablet structure. In yet another embodiment, the active agent/carrier component precursor may be a liquid formulation which is combined with the identifier and then solidified to produce the final composition. In yet other embodiments, pre-made tablets may be fitted with an identifier by stably attaching an identifier to the tablet. Of interest are protocols that do not alter the properties of the tablet, e.g., dissolution etc. For example, a gelatin element that snap fits onto one end of a tablet and has an identifier integrated with it is employed in certain embodiments. The gelatin element is colored in certain embodiments to readily identify tablets that have been fitted with the signal generation element. Where the composition has an active agent/carrier composition filled capsule configuration, e.g., such as a gelatin capsule filled configuration, an identifier may be integrated with a capsule component, e.g., top or bottom capsule, and the capsule filled with the active agent/carrier composition to produce the final composition. The above reviewed methods of manufacture are merely illustrative of the variety of different ways in which the compositions of the invention may be manufactured.

In certain embodiments, the identifiers are disrupted upon administration to a subject. As such, in certain embodiments, the compositions are physically broken, e.g., dissolved, degraded, eroded, etc., following delivery to a body, e.g., via ingestion, injection, etc. The compositions of these embodiments are distinguished from devices that are configured to be ingested and survive transit through the gastrointestinal tract substantially, if not completely, intact.

Systems

Also provided are systems that include the subject compositions. Systems of the subject invention include, in certain embodiments, one or more devices that include an in-body power source of the invention, e.g., an identifier as reviewed above, as well as a signal detection component, e.g., in the form of a receiver. The signal detection component may vary significantly depending on the nature of the signal that is generated by the signal generation element of the composition, e.g., as reviewed above.

Signal receivers of systems of embodiments of the invention are those that are configured to receive a signal from an identifier, e.g., to receive a signal emitted by an identifier upon contact of the identifier with the target physiological site following ingestion of the identifier. The signal receiver may vary significantly depending on the nature of the signal that is generated by the signal generation element, e.g., as reviewed below. As such, the signal receiver may be configured to receive a variety of different types of signals, including but not limited to: RF signals, magnetic signals, conductive (near field) signals, acoustic signals, etc., as indicated above. In certain embodiments, the receiver is configured to receive a signal conductively from another component, e.g., the identifier, such that the two components use the body of the patient as a communication medium. As such, the signal that is transferred between identifier o and the receiver travels through the body, and requires the body as the conduction medium. The identifier emitted signal may be transmitted through and received from the skin and other body tissues of the subject body in the form of electrical alternating current (a.c.) voltage signals that are conducted through the body tissues. As a result, such embodiments do not require any additional cable or hard wire connection, or even a radio link connection for transmitting the sensor data from the autonomous sensor units to the central transmitting and receiving unit and other components of the system, since the sensor data are directly exchanged via the skin and other body tissues of the subject. This communication protocol has the advantage that the receivers may be adaptably arranged at any desired location on the body of the subject, whereby the receivers are automatically connected to the required electrical conductor for achieving the signal transmission, i.e., the signal transmission is carried out through the electrical conductor provided by the skin and other body tissues of the subject. In certain embodiments, the signal detection component is one that is activated upon detection of a signal emitted from an identifier. In certain embodiments, the signal receiver is capable of (i.e., configured to) simultaneously detecting multiple different signals, e.g., 2 or more, 5 or more, 10 or more, etc.

The signal receiver may include a variety of different types of signal receiver elements, where the nature of the receiver element necessarily varies depending on the nature of the signal produced by the signal generation element. In certain embodiments, the signal receiver may include one or more electrodes (e.g., 2 or more electrodes, 3 or more electrodes, includes multiple, e.g., 2 or more, 3 or more, 4 or more pairs of electrodes, etc.) for detecting signal emitted by the signal generation element. In certain embodiments, the receiver device will be provided with two electrodes that are dispersed at a distance, e.g., a distance that allows the electrodes to detect a differential voltage. This distance may vary, and in certain embodiments ranges from about 0.1 to about 5 cm, such as from about 0.5 to about 2.5 cm, e.g., about 1 cm. In an alternative embodiment, a receiver that utilizes a single electrode is employed. In certain embodiments, the signal detection component may include one or more coils for detecting signal emitted by the signal generation element. In certain embodiments, the signal detection component includes an acoustic detection element for detecting signal emitted by the signal generation element. In certain embodiments, multiple pairs of electrodes (e.g., as reviewed above) are provided, for example to increase detection probability of the signal.

The signal receivers of interest include both external and implantable signal receivers. In external embodiments, the signal receiver is ex vivo, by which is meant that the receiver is present outside of the body during use. Where the receiver is implanted, the signal receiver is in vivo. The signal receiver is configured to be stably associated with the body, e.g., either in vivo or ex vivo, at least during the time that it receives the emitted signal from the IEM.

Signal receivers of interest include, but are not limited to, those receivers disclosed in: PCT application serial no. PCT/US2006/016370 filed on Apr. 28, 2006 and entitled PHARMA-INFORMATICS SYSTEM; and PCT application serial no. PCT/US2008/052845 filed on Feb. 1, 2008 and entitled INGESTIBLE EVENT MARKER SYSTEMS; the disclosures of which applications (and particularly signal receiver components thereof) are herein incorporated by reference.

In certain embodiments, the signal receiver is configured to provide data of a received signal to a location external to said subject. For example, the signal receiver may be configured to provide data to an external data receiver, e.g., which may be in the form of a monitor (such as a bedside monitor), a computer (e.g., PC or MAC), a personal digital assistant (PDA), phone, messaging device, smart phone, etc. In one embodiment, if a signal receiver failed to detect a signal indicating that a pill had been ingested, the signal receiver could transmit a reminder to take the pill to the subject's PDA or smart phone, which could then provide a prompt to the user to take the medication, e.g., a display or alarm on the PDA, by receiving a phone call on the smart phone (e.g., a recorded message) etc. The signal receiver may be configured to retransmit data of a received signal to the location external to said subject. Alternatively, the signal receiver according may be configured to be interrogated by an external interrogation device to provide data of a received signal to an external location.

As such, in certain embodiments the systems include an external device which is distinct from the receiver (which may be implanted or topically applied in certain embodiments), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, smart phones, home computers, etc. The device can read out the information described in more detail in other sections of the subject patent application, both from pharmaceutical ingestion reporting and from physiological sensing devices, such as is produced internally by a pacemaker device or a dedicated implant for detection of the pill. The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Methods

Aspects of the invention further include methods of using in-body devices that include in-body power sources of the invention. Generally, methods of the invention will include placing the in-body device in some manner in the body of the subject, e.g., by implanting the device in a subject, by ingesting the device, etc. The devices may be employed with a variety of subjects. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In certain embodiments, the subjects will be humans. Following placement of the devices in the body of a subject, the devices are employed for a variety of purposes, e.g., to sense one or more physiological parameters, to deliver one or more therapies, to mark a personal event of interest, etc.

In certain embodiments, the in body devices are ingestible devices, where the in body power source is part of an identifier of the device. In such embodiments, the identifier is ingested and a signal emitted by the identifier is detected, e.g., with a receiver as described above. Such methods are further described in PCT application serial no. PCT/US2006/016370 filed on Apr. 28, 2006 and entitled PHARMA-INFORMATICS SYSTEM; and PCT application serial no. PCT/US2008/052845 filed on Feb. 1, 2008 and entitled INGESTIBLE EVENT MARKER SYSTEMS; the disclosures of which applications (and particularly signal receiver components thereof) are herein incorporated by reference.

Utility

Devices that include the in-body power sources of the invention may be employed in a variety of different applications, including both therapeutic and non-therapeutic applications. Specific applications of interest include, but are not limited to: those applications described in PCT application serial no. PCT/US2006/016370 filed on Apr. 28, 2006 and entitled PHARMA-INFORMATICS SYSTEM; and PCT application serial no. PCT/US2008/052845 filed on Feb. 1, 2008 and entitled INGESTIBLE EVENT MARKER SYSTEMS; the disclosures of which applications (and particularly signal receiver components thereof) are herein incorporated by reference.

IEM in body devices of the invention may be employed in a variety of different applications, which applications may be both medical and non-medical in nature. Different illustrative applications are now reviewed below in greater detail below.

Certain applications involve the use of IEMs by themselves to mark a personal event of interest, e.g., onset of a physiological parameter (such as a symptom(s) of interest), onset of an activity, etc. For example, in certain embodiments, event markers are employed to mark the onset of a symptom of interest. In such instances, when an individual becomes aware of a symptom of interest, e.g., begins to feel flushed, nauseous, excited, etc., e.g., the individual may ingest an IEM to mark the occurrence of the symptom of interest. For example, the patient may begin to not feel well, and ingest an event marker in response to this ill feeling. Upon ingestion, the marker sends a signal to a receiver, which may then record receipt of the signal for further use, e.g., to combine with physiological data, etc. In certain embodiments, the received signal is employed to provide context for any physiological data that is obtained from the patient, e.g., by sensors on the receiver, from an implantable recorder, etc.

Another symptom of interest is pain. In these embodiments, the ingestible event marker may be employed a pain marker. For example, where a patient is being monitored for pain, if a patient feels no pain, the patient may ingest a first type of marker. If the patient feels pain, the patient may ingest a second type of marker. Different types of markers may be differentiated, such as color coded, where desired, to assist in their identification and proper use by the patient. For example, markers to be ingested when the patient does not feel pain may be color coded blue, while markers that are to be ingested with the patient does have pain may be color coded yellow. Instead of having different types of markers, a protocol may be employed in which the amount of markers ingested, and therefore the signal obtained, e.g., from a single marker or two or more markers, is employed to denote scale of symptom of interest, such as pain. So, if an individual is having intense pain, the individual takes four of the positive pain pills at the same time, while in response to mild pain the individual may take only one marker.

In such embodiments, the onset of the symptom of interest, as marked by the ingestion of the event marker and detection of the signal by the receiver, may be employed as relevant point at which to begin recording one or more physiological parameters of interest, e.g., by using an implantable physiological monitor. In these instances, the emitted signal from the marker is received by the receiver, which then causes a physiological parameter recorder (such as a Reveal® Plus Insertable Loop Recorder (ILR), Medtronic Corporation) to begin recording data and saving the data, e.g., for later use. For example, an implantable physiological parameter recorder may have only a limited possible amount of time for recording (such as 42 minutes). In such situations, the data may be automatically overwritten unless somehow flagged or marked for protection. In the present methods, an IEM may be ingested to mark the onset of a symptom of interest, as perceived by the patient, and receiver upon receipt of the signal may act with the recorder to protect the data obtained around the time of the signal (after, or even some time before) to be protected and not overwritten. The system may be further configured to work in response not only to the ingestion of the event marker, but also in response to physiological sensed parameters, e.g., pH. As such, the methods find use as an event recorder in terms of flagging a diagnostic stream of information, and protecting it from being overwritten, so a physician can look at it at a later date.

In certain embodiments, the event marker provides the context for interpreting a given set of physiological data at a later time. For example, if one is employing an activity sensor and one co-administers and event marker with a particular drug, one can note any change in activity that is brought about by that drug. If a drop in activity is observed after a person takes both the event marker and a drug, the drop indicates the drug is probably causing the person to reduce their activity, e.g., by making them feel sleepy or actually causing them to fall asleep. Such data may be employed to adjust the does of a drug or be the basis for a decision to switch to an alternative medication.

In certain embodiments the event marker is employed to construct a database of multiple events. Such a database may be employed to find commonality between the multiple marked events. Simple or complex protocols for finding commonality among multiple marked events may be employed. For example, multiple events may be averaged. Alternatively techniques such as impulse response theory may be employed, where such techniques provide information on what exactly are the common features in a set of multiple sensor streams that are tied to a particular event.

The IEM systems of the invention enable one to use subjective symptoms, such as "I'm feeling funny," to impart context and background to obtained objective measures of what's really going on physiologically. So, if every time somebody felt abnormal they took an event marker, one could reference a database of the objective sensor data, and find common features in the database. Such an approach may be employed to discover the underlying causes of the subjective feeling. For example, such an approach may be employed to determine that every time a person is feeling funny, they have some change in their blood pressure, and that link between a subjective symptom and objective physiological data can be used in their diagnosis. As such, a generalizable event marker brings context to discrete data from any other source. As such, use of the oral medication event markers provides context for any other associated health monitoring information or health event.

In certain embodiments, the event marker can be an alert marker, such that ingestion of the marker causes an alarm signal to be sent from the patient, e.g., indicating that the patient needs medical assistance. For example, when a patient feels an onset of a symptom of interest, such as chest pain, shortness of breath, etc., the patient may ingest an event marker. The signal emitted from the event marker may be received by the receiver, which may then cause an alarm to be generated and distributed to a medical professional.

In certain embodiments, the event marker is employed to instigate or start a therapeutic action, e.g., activate an implantable pulse generator to deliver electrical therapy, activate an implanted drug delivery device to administer a dosage of drug, activate a physiological sensor to begin acquiring data, etc. For example, where a patient has a neural stimulator for treating migraines, upon perception of the onset of aura, the patient could ingest an IEM. The emitted signal would then activate neural stimulator into stimulus mode, and thereby cause the implant to deliver therapy. Alternatively, if one has an implanted drug deliver device, e.g., a device that delivers an oncotic agent, ingestion of the IEM could cause the implanted device to deliver the active agent.

In certain embodiments, the event marker is employed to deliver information to an implanted medical device in the patient. For example, an ingestible event marker may send a signal that includes update data for an implanted medical devices, such as firmware upgrade data for an implantable pulse generator, e.g., a pace maker. In such instances, the signal may include the upgrade code which is broadcast from the IEM conductively to the medical device, where upon receipt of the signal and code, the firmware of the medical device is upgraded.

Other applications where event markers may be employed by themselves is to mark or note the start of non-medical personal event, such as a commute time, the start of an exercise regimen, sleep time, smoking (e.g., so one can log how much one smokes) etc.

As indicated above, embodiments of the invention are characterized in that the event markers are co-ingested with another composition of matter, e.g., a pharmaceutical composition, food, etc, where the event marker may or may not be present in the same composition as the co-ingested matter. For example, the event markers may be employed to track ingesting a pharmaceutical agent, where one co-administers the marker with the drug of interest. Applications where co-administration of a drug and marker is of interest include, but are not limited to, clinical studies, titration of medicine, e.g., blood pressure medicine, etc. Where desired, the IEM could be provided as just another pill when the fill at the pharmacy essentially.

Instead of co-ingesting the event marker with another composition, e.g., a drug, food, etc., the marker and the other composition may be compounded together, e.g., by the end user. For example, an IEM in the form of a capsule can be opened by the end user and filled with a pharmaceutical composition. The resultant compounded capsule and active agent may then be ingested by the end user. Instead of an end user, the pharmacist or a health care provided may perform the compounding step.

In yet other embodiments, the marker is present already compounded with the other composition at the source of manufacture of the other composition, e.g., the manufacturer or producer of a pharmaceutical composition. An example of such compositions includes those described in PCT application serial no. PCT/US2006/016370; the disclosure of which is herein incorporated by reference.

In certain embodiments, the IEMs of the invention are employed to allow one to look at, on an individual basis, what a given result is with respect to what drugs an individual is taking versus their impact on indicators that correlate to the desired effect. For example, where a given patient is prescribed a regiment of multiple pharmaceutical agents and there are multiple different physiological parameters that are monitored as indicators of how the patient is responding to the prescribed therapeutic regimen, a given drug as marked by a given marker can be assessed in terms of its impact on a one or more of the physiological parameters of interest. Following this assessment, adjustments can be made accordingly. In this manner, automation may be employed to tailor therapies based on individual responses. For example, where a patient is undergoing oncotic therapy, the event marker can be used to provide real time context to obtained physiological parameter data. The resultant annotated real time data can be used to make decisions about whether or not to continue therapy, or change to a new therapy. In certain embodiments, a dosing event (as marked by the IEM) is correlated with sensor data to develop a profile for how a given drug acts, e.g., in terms of a pharmacokinetic and/or pharmacodynamic model. Sensors are employed with the IEM marking of the dosing event to obtain a pharmacokinetic model. Once one has the pharmacokinetic model, one can use the dosing event to drive that model and predict serum drug levels and response. One might find, as determined from various sensors, that this patient is not doing so well at this time. One might look back at the pharmacokinetic model and say the levels of this drug in the blood are getting low when the patient is sensed as not doing well. This data is then used to make a determination to increase the dosing frequency or increase the dose at a given dosing event. The event marker provides a way to develop a model and then apply it.

Where the IEMs are co-administered with a pharmaceutical agent, e.g., as two separate compositions or a single composition (as described above), the systems of the invention, such as the one shown in FIG. 12, enable a dynamic feedback and treatment loop of tracking medication timing and levels, measuring the response to therapy, and recommending altered dosing based on the physiology and molecular profiles of individual patients. For example, a symptomatic heart failure patient takes multiple drugs daily, primarily with the goal of reducing the heart's workload and improving patient quality of life. Mainstays of therapy include angiotensin converting enzyme (ACE) inhibitors, β-blockers and diuretics. For pharmaceutical therapy to be effective, it is vital that patients adhere to their prescribed regimen, taking the required dose at the appropriate time. Multiple studies in the clinical literature demonstrate that more than 50% of Class II and III heart failure patients are not receiving guideline-recommended therapy, and, of those who are titrated appropriately, only 40-60% adhere to the regimen. With the subject systems, heart failure patients can be monitored for patient adherence to therapy, and adherence performance can be linked to key physiologic measurements, to facilitate the optimization of therapy by physicians.

In certain embodiments, the systems of the invention may be employed to obtain an aggregate of information that includes sensor data and administration data. For example, one can combine the heart rate, the respiration rate, multi-axis acceleration data, something about the fluid status, and something about temperature, and derive indices that will inform about the total activity of the subject, that can be used to generate a physiological index, such as an activity index. For instance, when there is a rise in temperature, heart rate goes up a bit, and respiration speeds up, which may be employed as an indication that the person is being active. By calibrating this, the amount of calories the person is burning at that instant could be determined. In another example, a particular rhythmic set of pulses or multi-axis acceleration data can indicate that a person is walking up a set of stairs, and from that one can infer how much energy they are using. In another embodiment, body fat measurement (e.g. from impedance data) could be combined with an activity index generated from a combination of measured biomarkers to generate a physiological index useful for management of a weight loss or cardiovascular health program. This information can be combined with cardiac performance indicators to get a good picture of overall health, which can be combined with pharmaceutical therapy administration data. In another embodiment, one might find for example that a particular pharmaceutical correlates with a small increase in body temperature, or a change in the electrocardiogram. One can develop a pharmacodynamic model for the metabolism of the drug, and use the information from the receiver to essentially fit the free parameters in that model to give much more accurate estimation of the levels actually present in the serum of the subject. This information could be fed back to dosing regimes. In another embodiment, one can combine information from a sensor that measures uterine contractions (e.g. with a strain gauge) and that also monitors fetal heart rate, for use as a high-risk pregnancy monitor.

In certain embodiments, the subject specific information that is collected using the systems of the invention may be transmitted to a location where it is combined with data from one or more additional individuals to provide a collection of data which is a composite of data collected from 2 or more, e.g., 5 or more, 10 or more, 25 or more, 50 or more, 100 or more, 1000 or more, etc., individuals. The composite data can then be manipulated, e.g., categorized according to different criteria, and made available to one or more different types of groups, e.g., patient groups, health care practitioner groups, etc., where the manipulation of data may be such as to limit the access of any given group to the type of data that group can access. For example, data can be collected from 100 different individuals that are suffering from the same condition and taking the same medication. The data can be processed and employed to develop easy to follow displays regarding patient compliance with a pharmaceutical dosage regimen and general health. Patient members of the group can access this information and see how their compliance matches with other patient members of the group, and whether they are enjoying the benefits that others are experiencing. In yet another embodiment, doctors can also be granted access to a manipulation of the composite data to see how their patients are matching up with patients of other doctors, and obtain useful information on how real patients respond to a given therapeutic treatment regiment. Additional functionalities can be provided to the groups given access to the composite data, where such functionalities may include, but are not limited to: ability to annotate data, chat functionalities, security privileges, etc.

The inventive pharmacokinetic model allows for drug dosing regimens to be adjusted in real time in response to varying serum levels in the body. The pharmacokinetic model can predict or measure the serum level of a given medication in the body. This data can then be used to calculate when the next dose of medication should be taken by the patient. An alarm can be triggered at that time to alert the patient to take a dose. If the serum level remains high, an alarm can be triggered to alert the patient not to take the next dose at the originally prescribed time interval. The pharmacokinetic model can be used in conjunction with a medication ingestion monitoring system that includes an IEM, such as that described above. Data from this system can be incorporated into the model, as well as population data, measured data, and data input by the patient. Utilizing data from multiple sources, a very powerful and accurate tool can be developed.

In some embodiments, the data gathered by the receiver can be used directly by the pharmacokinetic model to determine when a medication was administered, what medication it was and in what amount. This information can be used to calculate an estimate of the serum level of the medication in the patient. Based on the calculated serum level, the pharmacokinetic model can send an alert to the patient to say either that the serum level is too high and is near or above the toxic level, or that the serum level is too low and they should take another dose. The pharmacokinetic model can be run on the implanted receiver itself or on an external system which receives data from the implanted receiver.

A simple form of the pharmacokinetic model can assume that every patient is the same, and use average population data to model the serum level. A more complex and more accurate model can be obtained by inputting other information about the patient. This information can be inputted by the user, such as a physician, or gathered by the receiver from associated sensors. Information that can be used to adjust the model include other medications being taken, diseases the patient suffers from, patient's organ function, enzyme levels, metabolism, body weight, and age, among other factors. Information can also be inputted by the patient themselves, such as if they feel hypoglycemic, or have pain or dizziness. This can be used as further evidence to validate the predictions of the model.

Examples of food applications include the following. In certain disease conditions, such as diabetes, it can be important what a patient ate and when. In such instances, event markers of the invention are keyed or linked to the type of food a patient eats. For example, one can have a set of event markers for different food items, and one can co-administer them with the food items. From the resultant data, one can do a complete individual metabolic profile on an individual. One knows how many calories the patient is consuming. By obtaining activity and heart rate and ambient temperature versus body temperature data, one can calculate how many calories one is expending. As a result, guidance can be provided to the patient as to what foods to eat and when. Non disease patients may also track food ingestion in this manner. For example, athletes adhering to a strict training diet may employ IEMs to better monitor food ingestion and the effect of the food ingestion on one or more physiological parameters of interest.

As reviewed in the above discussion, IEM systems of the invention find use in both therapeutic and non-therapeutic applications. In therapeutic applications, the IEM may or may not be compounded with a pharmaceutically active agent. In those embodiments where the IEM is compounded with active agent, the resultant compounded composition may be viewed as a pharma-informatics enabled pharmaceutical composition.

In such pharma-informatics embodiments, an effective amount of a composition that includes an IEM and an active agent is administered to a subject in need of the active agent present in the composition, where "effective amount" means a dosage sufficient to produce the desired result, e.g. an improvement in a disease condition or the symptoms associated therewith, the accomplishment of a desired physiological change, etc. The amount that is administered may also be viewed as a therapeutically effective amount. A "therapeutically effective amount" means the amount that, when administered to a subject for treating a disease, is sufficient to effect treatment for that disease.

The composition may be administered to the subject using any convenient means capable of producing the desired result, where the administration route depends, at least in part, on the particular format of the composition, e.g., as reviewed above. As reviewed above, the compositions can be formatted into a variety of formulations for therapeutic administration, including but not limited to solid, semi solid or liquid, such as tablets, capsules, powders, granules, ointments, solutions, suppositories and injections. As such, administration of the compositions can be achieved in various ways, including, but not limited to: oral, buccal, rectal, parenteral, intraperitoneal, intradermal, transdermal, intracheal, etc., administration. In pharmaceutical dosage forms, a given composition may be administered alone or in combination with other pharmaceutically active compounds, e.g., which may also be compositions having signal generation elements stably associated therewith.

The subject methods find use in the treatment of a variety of different conditions, including disease conditions. The specific disease conditions treatable by with the subject compositions are as varied as the types of active agents that can be present in the subject compositions. Thus, disease conditions include, but are not limited to: cardiovascular diseases, cellular proliferative diseases, such as neoplastic diseases, autoimmune diseases, hormonal abnormality diseases, infectious diseases, pain management, and the like.

By treatment is meant at least an amelioration of the symptoms associated with the disease condition afflicting the subject, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition. Accordingly, "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

In certain embodiments, the subject methods, as described above, are methods of managing a disease condition, e.g., over an extended period of time, such as 1 week or longer, 1 month or longer, 6 months or longer, 1 year or longer, 2 years or longer, 5 years or longer, etc. The subject methods may be employed in conjunction with one or more additional disease management protocols, e.g., electrostimulation based protocols in cardiovascular disease management, such as pacing protocols, cardiac resynchronization protocols, etc; lifestyle, such a diet and/or exercise regimens for a variety of different disease conditions; etc.

In certain embodiments, the methods include modulating a therapeutic regimen based data obtained from the compositions. For example, data may be obtained which includes information about patient compliance with a prescribed therapeutic regimen. This data, with or without additional physiological data, e.g., obtained using one or more sensors, such as the sensor devices described above, may be employed, e.g., with appropriate decision tools as desired, to make determinations of whether a given treatment regimen should be maintained or modified in some way, e.g., by modification of a medication regimen and/or implant activity regimen. As such, methods of invention include methods in which a therapeutic regimen is modified based on signals obtained from the composition(s).

In certain embodiments, also provided are methods of determining the history of a composition of the invention, where the composition includes an active agent, an identifier element and a pharmaceutically acceptable carrier. In certain embodiments where the identifier emits a signal in response to an interrogation, the identifier is interrogate, e.g., by a wand or other suitable interrogation device, to obtain a signal. The obtained signal is then employed to determine historical information about the composition, e.g., source, chain of custody, etc.

In certain embodiments, a system is employed that is made up of a multiple different IEMs, e.g., 2 or more distinct IEMS, 3 or more distinct IEMS, 4 or more distinct IEMs, etc., including 5 or more, 7 or more, 10 or more distinct IEMs. The distinct IEMs may be configured to provide distinguishable signals, e.g., where the signals may be distinguishable in terms of nature of the signal itself, in terms of timing of emission of the signal, etc. For example, each IEM in such sets may emit a differently coded signal. Alternatively, each IEM may be configured to emit the signal at a different physiological target site, e.g., where each IEM is configured to be activated at a different target physiological site, e.g., where an first IEM is activated in the mouth, a second is activated in the esophagus, a third is activated in the small intestine and a fourth is activated in the large intestine. Such sets of multiple different distinguishable IEMs find use in a variety of different applications. For example, where one has the above described 4 IEM set, one can use the set in a diagnostic application to determine function of the digestive system, e.g., motility through the digestive tract, gastric emptying etc. For example, by noting when each IEM emits its respective signal, a plot of signal time may be generated from which information regarding digestive tract functioning may be obtained.

The present invention provides the clinician an important new tool in their therapeutic armamentarium: automatic detection and identification of pharmaceutical agents actually delivered into the body. The applications of this new information device and system are multi-fold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is reviewed in greater detail below in copending PCT Application Serial No. PCT/US2006/016370; the disclosure of which is herein incorporated by reference.

Additional applications in which the subject systems find use include those described in U.S. Pat. No. 6,804,558, the disclosure of which is herein incorporated by reference. For example, the subject systems may be used in a medical information communication system which permits monitoring the performance of an implantable medical device (IMD) implanted within a body of a patient, monitoring the health of the patient, and/or remotely delivering a therapy to the patient through the IMD. A signal receiver of the invention, e.g., in an external format such as a bandaid or implanted format, communicates with the IMD and is capable of bi-directional communication with a communication module, a mobile telephone and/or a Personal Data Assistant (PDA) located outside the patient's body. The system may comprise the IMD, the signal receiver with the communication module and/or a mobile telephone and/or a PDA, a remote computer system, and a communication system capable of bi-directional communication, where the communication module, the mobile telephone and/or the PDA are capable of receiving information from the IMD or relaying information thereto via the signal receiver, which is internal or external to the patient, as reviewed above.

Additional applications in which receivers of the invention may find use include, but are not limited to: fertility monitoring, body fat monitoring, satiety monitoring, satiety control, total blood volume monitoring, cholesterol monitoring, smoking detecting, etc.

Kits

Also provided are kits that include one or more in-body devices of the invention. Kits may include one or more in-body devices, e.g., as described above. In those embodiments having multiple in body devices, such may be packaged in a single container, e.g., a single tube, bottle, vial, and the like, or one or more dosage amounts may be individually packaged such that certain kits may have more than one container of an in body device. In certain embodiments the kits may also include a signal receiving element, as reviewed above. In certain embodiments, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Certain ranges have been presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An in-body medical device comprising:

an integrated circuit substrate comprising a surface and a circuitry element;

a first electrode coupled to the circuitry element and comprising:

a first active electrode material;

a first surface; and a second surface;

a second electrode connected to the surface of the integrated circuit substrate and coupled to the circuitry element, wherein the second electrode is electrically isolated from the first electrode and comprises a second active electrode material that is different from the first active electrode material; and an electrically conductive porous under-layer interposed between the first surface of the first electrode and the surface of the integrated circuit substrate, the electrically conductive porous under-layer comprising an inert metal or an oxidizable metal; wherein the electrically conductive porous under-layer is configured to provide a surface area enhancement to the first electrode, wherein the electrically conductive porous under-layer is configured to improve adhesion, and wherein the electrically conductive porous under-layer is a layer that is contiguous to and mechanically supports the first electrode; and wherein the in-body medical device is suitable for human ingestion or implantation.

2. The in-body medical device according to claim 1, wherein the device is dimensioned to be ingestible.

3. The in-body medical device according to claim 1, wherein the electrically conductive porous under-layer comprises an element selected from the group consisting of: Au, Cu, Pt, Ir, Pd, Rh and Ru and alloys thereof.

4. The in-body medical device according to claim 1, wherein the electrically conductive porous under-layer comprises an element selected from the group consisting of: Ti and W and alloys thereof.

5. The in-body medical device according to claim 1, wherein the electrically conductive porous under-layer has a thickness ranging from 0.1 to 100 μm.

6. The in-body medical device according to claim 1, wherein the first electrode is formed on the same surface of the integrated circuit substrate as the second electrode.

7. The in-body medical device according to claim 1, wherein:

the surface of the integrated circuit substrate comprises a first substrate surface to which the first electrode is connected via the electrically conductive porous under-layer and a second substrate surface to which the second electrode is connected; and the first substrate surface is arranged opposite to the second substrate surface.

8. The in-body medical device according to claim 1, wherein the device comprises a pharmaceutically acceptable carrier composition.

9. The in-body medical device according to claim 8, wherein the pharmaceutically acceptable carrier composition is in the form of a tablet.

10. The in-body medical device according to claim 8, wherein the pharmaceutically acceptable carrier composition is in the form of a capsule.

11. The in-body medical device according to claim 8, wherein the pharmaceutically acceptable carrier composition comprises an active agent.

12. The device of claim 1, wherein the second surface is uncovered by the electrically conductive porous under-layer.

13. A system comprising:

a receiver; and an in-body medical device suitable for human ingestion or implantation, wherein the in- body medical device is configured to communicate with the receiver, the in-body medical device comprising:

an integrated circuit substrate comprising a surface and a circuitry element;

a first electrode coupled to the circuitry element and comprising:

a first active electrode material;

a first surface; and a second surface;

a second electrode connected to the surface of the integrated circuit substrate and coupled to the circuitry element, wherein the second electrode is electrically isolated from the first electrode and comprises a second active electrode material that is different from the first active electrode material; and an electrically conductive porous under-layer interposed between the first surface of the first electrode and the surface of the integrated circuit substrate, the electrically conductive porous under-layer comprising an inert metal or an oxidizable metal; wherein the electrically conductive porous under-layer is configured to provide a surface area enhancement to the first electrode, wherein the electrically conductive porous under-layer is configured to improve adhesion, and wherein the electrically conductive porous under-layer is a layer that is contiguous to and mechanically supports the first electrode.

14. The system according to claim 13, wherein said receiver is an in vivo receiver.

15. The system according claim 13, wherein said receiver is an ex vivo receiver.

16. The system according to claim 13, wherein the electrically conductive porous under-layer is provided by electrodeposition.

17. The system according to claim 13, wherein the electrically conductive porous under-layer is provided by cathodic arc deposition.

18. The system according to claim 13, wherein the electrically conductive porous under-layer is provided by electrophoretic deposition.

19. The system of claim 13, wherein the second surface is uncovered by the electrically conductive porous under-layer.

* * * * *

UNITED STATES PATENT AND TRADEMARK OFFICE

CERTIFICATE OF CORRECTION

PATENT NO. : 11,464,423 B2
APPLICATION NO. : 14/602895
DATED : October 11, 2022
INVENTOR(S) : Hafezi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1098 days.

Signed and Sealed this
Eleventh Day of February, 2025

Coke Morgan Stewart
*Acting Director of the United States Patent and Trademark Office*